US012564179B2

(12) United States Patent　　　(10) Patent No.:　US 12,564,179 B2
Mirsaeidi et al.　　　　　　　　　(45) Date of Patent:　Mar. 3, 2026

(54) METHODS OF PRODUCING GRANULOMAS AND ANIMAL MODELS OF SARCOIDOSIS

(71) Applicants: UNITED STATES GOVERNMENT AS REPRESENTED BY THE DEPARTMENT OF VETERANS AFFAIRS, Washington, DC (US); UNIVERSITY OF MIAMI, Miami, FL (US)

(72) Inventors: Mehdi Mirsaeidi, Miami, FL (US); Chongxu Zhang, Miami, FL (US)

(73) Assignees: UNITED STATES GOVERNMENT AS REPRESENTED BY THE DEPARTMENT OF VETERANS AFFAIRS, Washington, DC (US); UNIVERSITY OF MIAMI, Miami, FL (US)

( * ) Notice: Subject to any disclaimer, the term of this patent is extended or adjusted under 35 U.S.C. 154(b) by 1015 days.

(21) Appl. No.: 17/623,382

(22) PCT Filed: Jun. 26, 2020

(86) PCT No.: PCT/US2020/039761
§ 371 (c)(1),
(2) Date: Dec. 28, 2021

(87) PCT Pub. No.: WO2020/264258
PCT Pub. Date: Dec. 30, 2020

(65) Prior Publication Data
US 2022/0361461 A1　　Nov. 17, 2022

Related U.S. Application Data

(60) Provisional application No. 62/868,129, filed on Jun. 28, 2019.

(51) Int. Cl.
A01K 67/02　　　(2006.01)
(52) U.S. Cl.
CPC .......... A01K 67/02 (2013.01); A01K 2207/10 (2013.01); A01K 2227/105 (2013.01); A01K 2267/0331 (2013.01)
(58) Field of Classification Search
None
See application file for complete search history.

(56) References Cited

U.S. PATENT DOCUMENTS

2009/0175798 A1　7/2009　Moller et al.
2015/0157701 A1　6/2015　Drancourt et al.

OTHER PUBLICATIONS

Abel B, et al., Toll-like receptor 4 expression is required to control chronic Mycobacterium tuberculosis infection in mice; J Immunol 2002; 169: 3155-3162.
Arredouani MS, et al., Is the scavenger receptor Marco a new immune checkpoint? Oncoimmunology 2014; 3(10): e955709.
Baechler EC, et al., Interferon-inducible gene expression signature in peripheral blood cells of patients with severe lupus; Proceedings of the National Academy of Sciences of the United States of America 2003; 100(5): 2610-2615.
Baughman RP, et al., A retrospective pilot study examining the use of Acthar gel in sarcoidosis patients; Respiratory medicine 2016; 110: 66-72.
Benjannet S, et al., PC1 and PC2 are proprotein convertases capable of cleaving proopiomelanocortin at distinct pairs of basic residues; Proceedings of the National Academy of Sciences of the United States of America 1991; 88(9): 3564-3568.
Bowdish DM, et al., Marco, TLR2, and CD14 are required for macrophage cytokine responses to mycobacterial trehalose dimycolate and Mycobacterium tuberculosis; PLoS pathogens 2009; 5(6): e1000474.
Brownell I, et al., Evidence for mycobacteria in sarcoidosis; American journal of respiratory cell and molecular biology, 2011; 45(5): 899-905.
Brzoska T, et al., Alpha-melanocyte-stimulating hormone and related tripeptides: biochemistry, antiinflammatory and protective effects in vitro and in vivo, and future perspectives for the treatment of immune-mediated inflammatory diseases; Endocr Rev 2008; 29(5): 581-602.
Catania A, et al., alpha-Melanocyte stimulating hormone in the modulation of host reactions; Endocr Rev 1993; 14(5): 564-576.
Chen ES, et al., Sarcoidosis—scientific progress and clinical challenges; Nat Rev Rheumatol 2011; 7(8): 457-467.
Chen et al. Serum Amyloid A Regulates Granulomatous Inflammation in Sarcoidosis through Toll-like Receptor-2; Am J Respir Crit Care Med, Nov. 12, 2009 (Nov. 12, 2009), vol. 181, pp. 360-373.
Chen ES, et al., Serum amyloid A regulates granulomatous inflammation in sarcoidosis through Toll-like receptor-2; American journal of respiratory and critical care medicine 2010; 181(4): 360-373.
Chen ES, et al., Etiology of sarcoidosis; Clinics in chest medicine, 2008; 29(3): 365-377.
Chhajlani V, et al., Molecular cloning of a novel human melanocortin receptor; Biochemical and biophysical research communications 1993; 195(2): 866-873.
Colombo G, et al., Anti-inflammatory effects of alpha-melanocyte-stimulating hormone in celiac intestinal mucosa; Neuroimmunomodulation 2002; 10(4): 208-216.
Crouser ED, et al., A Novel In Vitro Human Granuloma Model of Sarcoidosis and Latent Tuberculosis Infection; American journal of respiratory cell and molecular biology 2017; 57(4): 487-498.
Cutuli M, et al., Antimicrobial effects of alpha-MSH peptides; Journal of leukocyte biology 2000; 67(2): 233-239.

(Continued)

*Primary Examiner* — Brian Gangle
(74) *Attorney, Agent, or Firm* — BALLARD SPAHR LLP

(57)　　　ABSTRACT

The disclosure relates to a sarcoidosis animal model and methods of inducing sarcoidosis in an animal. The disclosure also relates to methods of producing an in vitro granuloma, and methods of using the sarcoidosis animal model. Disclosed herein are animals comprising one or more granulomas, wherein the one or more granulomas comprise *Mycobacterium abscessus* cell wall microparticles.

8 Claims, 18 Drawing Sheets
Specification includes a Sequence Listing.

(56)          References Cited

OTHER PUBLICATIONS

Decaris ML, et al., Proteomic analysis of altered extracellular matrix turnover in bleomycin-induced pulmonary fibrosis; Mol Cell Proteomics. (2014) 13(7):1741-52.

Drake WP, et al., Cellular recognition of Mycobacterium tuberculosis ESAT-6 and KatG peptides in systemic sarcoidosis; Infection and immunity 2007; 75(1): 527-530.

Dubaniewicz A, et al., Mycobacterium tuberculosis complex and mycobacterial heat shock proteins in lymph node tissue from patients with pulmonary sarcoidosis; J Clin Microbiol 2006; 44(9): 3448-3451.

Eishi Y, et al., Quantitative analysis of mycobacterial and propionibacterial DNA in lymph nodes of Japanese and European patients with sarcoidosis; J Clin Microbiol 2002; 40(1): 198-204.

Fang C, et al., Immunological Evidence for the Role of Mycobacteria in Sarcoidosis: A Meta-Analysis; PloS one 2016; 11(8):e0154716.

Facco M, et al., Sarcoidosis is a Th1/Th17 multisystem disorder. Thorax 2011; 66(2): 144-150.

Gabrilovich MI, et al., Disordered Toll-like receptor 2 responses in the pathogenesis of pulmonary sarcoidosis; Clinical and experimental immunology 2013; 173(3): 512-522.

Gantz I, et al., The melanocortin system; Am J Physiol Endocrinol Metab 2003; 284(3): E468-474.

Green U, et al., Development and validation of a drug activity biomarker that shows target inhibition in cancer patients receiving enzastaurin, a novel protein kinase C-beta inhibitor; Clinical cancer research; 2006; 12: 3408-3415.

Griffith DE, et al., An official ATS/IDSA statement: diagnosis, treatment, and prevention of nontuberculous mycobacterial diseases; Am J Respir Crit Care Med. (2007) 175(4):367-416.

Guirado E, et al., Characterization of host and microbial determinants in individuals with latent tuberculosis infection using a human granuloma model; mBio 2015; 6(1): e02537-02514.

Hajizadeh R, et al., Mycobacterium tuberculosis Antigen 85A induces Th-1 immune responses in systemic sarcoidosis; Journal of clinical immunology 2007; 27(4): 445-454.

Herndon B, et al., Urease and *Helicobacter* spp. antigens in pulmonary granuloma; J Comp Pathol 2013; 148: 266-277.

Huizar I, et al., The role of PPARγ in carbon nanotube-elicited granulomatous lung inflammation; Respiratory research 2013; 14(1): 7.

Iannuzzi MC, et al., Sarcoidosis: clinical presentation, immunopathogenesis, and therapeutics; JAMA, 2011; 305(4): 391-399.

Iannuzzi MC, et al., Sarcoidosis; N Engl J Med 2007; 357(21): 2153-2165.

Ichikawa H, et al., Quantitative analysis of propionibacterial DNA in bronchoalveolar lavage cells from patients with sarcoidosis; Sarcoidosis Vase Diffuse Lung Dis; 2008; 259(1): 15-20.

Kawai T, et al., Signaling to NF-kappaB by Toll-like receptors; Trends Mol Med 2007; 13(11): 460-469.

Kalliolias GD, et al. Overview of the biology of type I interferons; Arthritis Res Ther. (2010) 12 (Suppl. 1):S1.

Kim et al. "Phagosome Escape of Rough Mycobacterium abscessus Strains in Murine Macrophage via Phagosomal Rupture Can Lead to Type I Interferon Production and Their Cell-To-Cell Spread," Front Immunol, Jan. 31, 2019 (Jan. 31, 2019), vol. 10, 125, pp. 1-18.

Kishi J, et al., Blockade of Th1 chemokine receptors ameliorates pulmonary granulomatosis in mice; The European respiratory journal 2011; 38(2): 415-424.

Kissick HT, et al., The scavenger receptor MARCO modulates TLR-induced responses in dendritic cells; PloS one 2014; 9(8): e104148.

Koh TJ, et al., Inflammation and wound healing: the role of the macrophage; Expert Rev Mol Med 2011; 13: e23.

Korukonda Azc, et al., Electronic Cigarettes Enhance Replication of Mycobacterium abscessus in Airway Epithelial Cells; Am J Respir Cell Mol Biol. (2019) 60(6):717-9.

Kucera GP, et al., Occupational risk factors for sarcoidosis in African-American siblings; Chest 2003; 123(5):1527-1535.

Kunzi L, et al., Cigarette smoke activates the parthanatos pathway of cell death in human bronchial epithelial cells; Cell Death Discov. (2019) 5:127.

Lazarus A. et al., Sarcoidosis: epidemiology, etiology, pathogenesis, and genetics; Dis Mon 2009; 55(11): 649-660.

Li J, et al., The Molecule Pages database; Nature 2002; 420: 716-717.

Lipton JM, et al., Anti-inflammatory actions of the neuroimmunomodulator alpha-MSH; Immunol Today 1997; 18(3): 140-145.

Lockstone HE, et al., Gene set analysis of lung samples provides insight into pathogenesis of progressive, fibrotic pulmonary sarcoidosis; American journal of respiratory and critical care medicine 2010; 181(12): 1367-1375.

Luger TA, et al., alpha-MSH related peptides: a new class of anti-inflammatory and immunomodulating drugs; Annals of the rheumatic diseases 2007; 66 Suppl 3: iii52-55.

Luthra S, et al., The Role of Antibiotic-Target-Modifying and Antibiotic-Modifying Enzymes in Mycobacterium abscessus Drug Resistance; Front Microbiol. (2018) 9:2179.

Matsuyama M, et al., Transcriptional Response of Respiratory Epithelium to Nontuberculous Mycobacteria; Am J Respir Cell. Mol Biol. (2018) 58(2):241-52.

Miller MA, et al., Effect of Acthar-c (ACTH) in sarcoidosis; Ann Intern Med 1952; 37(4): 776-784.

Minami J, et al., Pulmonary granulomas caused experimentally in mice by a recombinant trigger-factor protein of Propionibacterium acnes; J Med Dent Sci 2003; 50(4): 265-274.

Mirsaeidi M, et al., Racial difference in sarcoidosis mortality in the United States; Chest 2015; 147(2): 438-449.

Mirsaeidi M, et al., Metabolomics: Applications and Promise in Mycobacterial Disease; Ann Am Thorac Soc. (2015) 12(9): 1278-87.

Monack DM, et al., Persistent bacterial infections: the interface of the pathogen and the host immune system; Nat Rev Microbiol. (2004) 2(9):747-65.

Mukhopadhyay S, et al., SR-A/MARCO—mediated ligand delivery enhances intracellular TLR and NLR function, but ligand scavenging from cell surface limits TLR4 response to pathogens; Blood 2011; 117(4): 1319-1328.

Nagai S, et al., Outcome of sarcoidosis; Clinics in chest medicine 2008; 29(3): 565-574.

Newman LS, et al., A case control etiologic study of sarcoidosis: environmental and occupational risk factors; American journal of respiratory and critical care medicine 2004; 170(12): 1324-1330.

Nishida T, et al., Anti-inflammatory effects of alpha-melanocyte-stimulating hormone against rat endotoxin-induced uveitis and the time course of inflammatory agents in aqueous humor; International immunopharmacology 2004; 4(8): 1059-1066.

Nishiwaki T, et al., Indigenous pulmonary Propionibacterium acnes primes the host in the development of sarcoid-like pulmonary granulomatosis in mice; The American journal of pathology 2004; 165(2): 631-639.

Novikov A, et al., Mycobacterium tuberculosis triggers host type I IFN signaling to regulate IL-1β production in human macrophages; J Immunol. (2011) 187(5):2540-7.

Nunes H, et al., Sarcoidosis; Orphanet J Rare Dis 2007; 2: 46.

Oswald-Richter KA, et al., Dual analysis for mycobacteria and propionibacteria in sarcoidosis BAL; Journal of clinical immunology 2012; 32(5): 1129-1140.

Oswald-Richter KA, et al., Cellular responses to mycobacterial antigens are present in bronchoalveolar lavage fluid used in the diagnosis of sarcoidosis; Infection and immunity 2009; 77(9): 3740-3748.

Patterson KC, et al., Pulmonary fibrosis in sarcoidosis. Clinical features and outcomes; Annals of the American Thoracic Society 2013; 10(4): 362-370.

Prasse A, et al., Th1 cytokine pattern in sarcoidosis is expressed by bronchoalveolar CD4+ and CD8+ T cells; Clinical and experimental immunology 2000; 122(2): 241-248.

Randell SH, et al., Isolation and culture of airway epithelial cells from chronically infected human lungs; In vitro Cell Dev Biol Anim. (2001) 37(8):480-9.

(56) References Cited

OTHER PUBLICATIONS

Reuschl AK, et al., Innate activation of human primary epithelial cells broadens the host response to Mycobacterium tuberculosis in the airways; PLoS Pathog. (2017) 13(9):e1006577.

Rosenbaum DM, et al., The structure and function of G-protein-coupled receptors; Nature 2009; 459: 356-363.

Rutherford RM, et al., Mycobacteria in pathogenesis of sarcoidosis; Chest 2004; 125(1): 354.

Samokhin AO, et al., ApoE-deficient mice on cholate-containing high-fat diet reveal a pathology similar to lung sarcoidosis; Am J Pathol 2010; 176(3): 1148-1156.

Schurmann M, et al. Study of Toll-like receptor gene loci in sarcoidosis; Clinical and experimental immunology 2008; 152(3): 423-431.

Seaton ME, et al., Melanocortin-1 Receptor Polymorphisms and the Risk of Complicated Sepsis After Trauma: A Candidate Gene Association Study; Shock 2017; 47(1): 79-85.

Shamaei M PM, et al., The presence of mycobacterial antigens in sarcoidosis associated granulomas; Sarcoidosis Vasculitis and Diffuse Lung Disease 2017; 34(3): 236-241.

Shaywitz AJ and Greenberg ME. CREB: a stimulus-induced transcription factor activated by a diverse array of extracellular signals; Annual review of biochemistry 1999; 68: 821-861.

Swaisgood CM, et al., Development of a sarcoidosis murine lung granuloma model using Mycobacterium superoxide dismutase A peptide; American journal of respiratory cell and molecular biology 2011; 44(2): 166-174.

Taherzadeh S,et al., alpha-MSH and its receptors in regulation of tumor necrosis factor-alpha production by human monocyte/macrophages; The American journal of physiology 1999; 276(5): R1289-1294.

Tian et al. "Development of a Sarcoidosis-Like Granuloma in Vitro Model Using Peripheral Blood Mononuclear Cells of Patients with Sarcoidosis," American Thoracic Society International Conference, Poster Abstract, May 19, 2019 (May 19, 2019).

Tsiligianni I, et al., Th1/Th2 cytokine pattern in bronchoalveolar lavage fluid and induced sputum in pulmonary sarcoidosis; BMC pulmonary medicine 2005; 5: 8.

Valencia-Gattas M, et al., Gefitinib, an EGFR Tyrosine Kinase inhibitor, Prevents Smoke-Mediated Ciliated Airway Epithelial Cell Loss and Promotes Their Recovery; PLoS One. (2016) 11(8):e0160216.

Vu A, et al., Toll-like receptors in mycobacterial infection; Eur J Pharmacol 2017; 808: 1-7.

Wen AY, et al., The role of the transcription factor CREB in immune function; Journal of immunology 2010; 185(11): 6413-6419.

Yang Y. et al., Structure, function and regulation of the melanocortin receptors; Eur J Pharmacol 2011; 660(1): 125-130.

Zhang S, et al., Growth factors secreted by bronchial epithelial cells control myofibroblast proliferation: an in vitro co-culture model of airway remodeling in asthma; Laboratory investigation; a journal of technical methods and pathology 1999; 79(4): 395-405.

Zhang et al. "Mycobacterium abscessus-Bronchial Epithelial Cells Cross-Talk Through Type I Interferon Signaling," Front Immunol, Dec. 9, 2019 (Dec. 9, 2019), vol. 10, 2888, pp. 1-9.

Zhang et al. "Anti-inflammatory effects of a-MSH through p-CREB expression in sarcoidosis like granuloma model," Sci Rep, Apr. 29, 2020 (Apr. 29, 2020), vol. 10, 7277, pp. 1-12.

International Search Report and Written Opinion were mailed on Sep. 30, 2020 by the International Searching Authority for International Application No. PCT/US2020/039761, filed on Jun. 26, 2020 and published as WO/2020/264258 on Dec. 30, 2020 (Applicant—United States Government as represented by The Department of Veterans Affairs) (83 Pages).

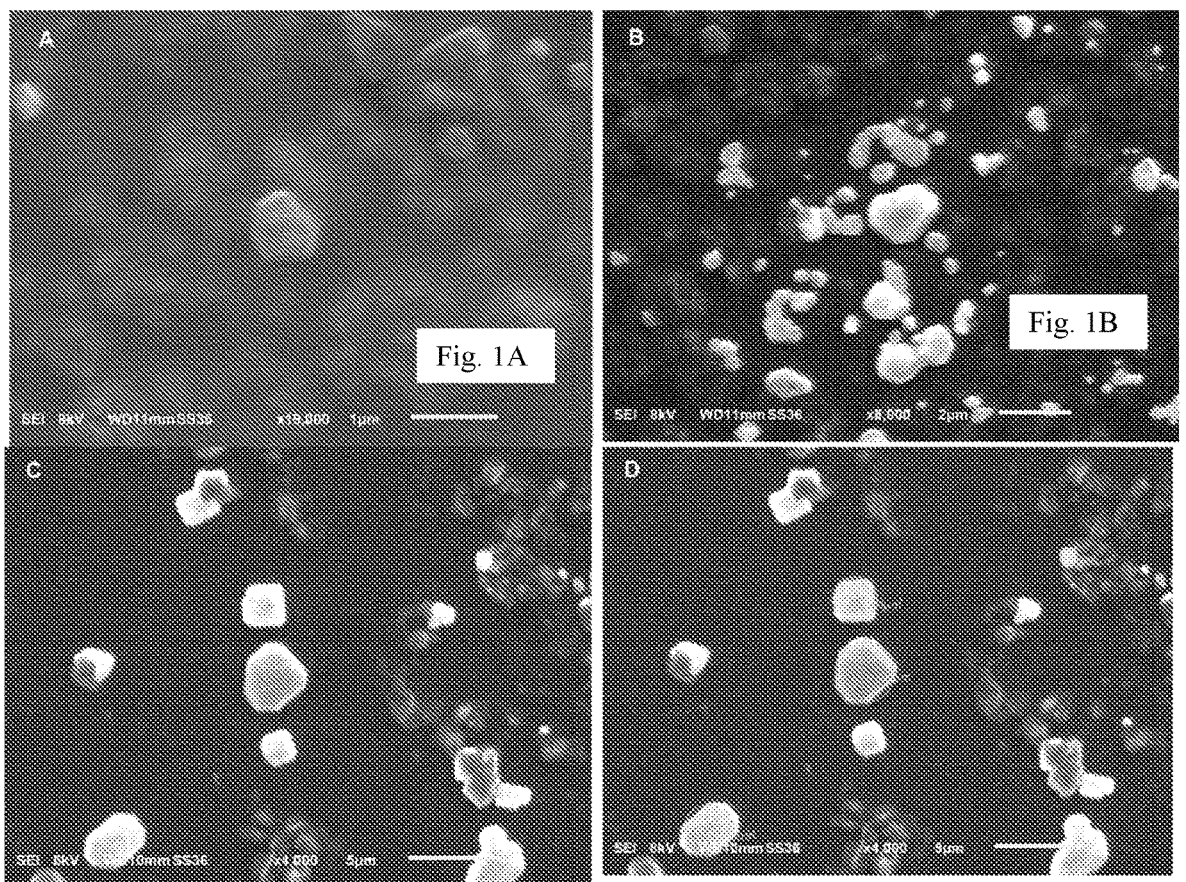
Fig. 1C                                    Fig. 1D

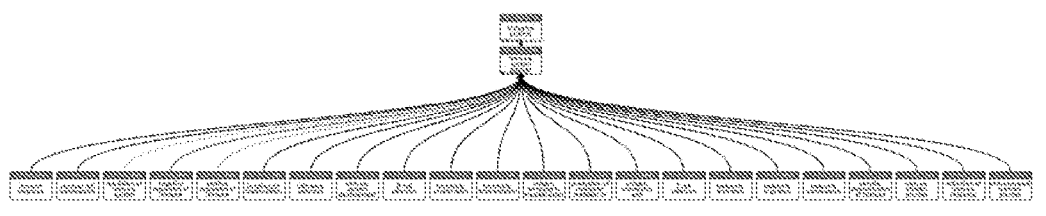
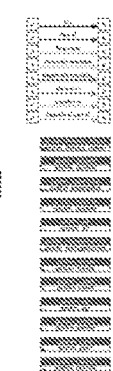
FIG. 11
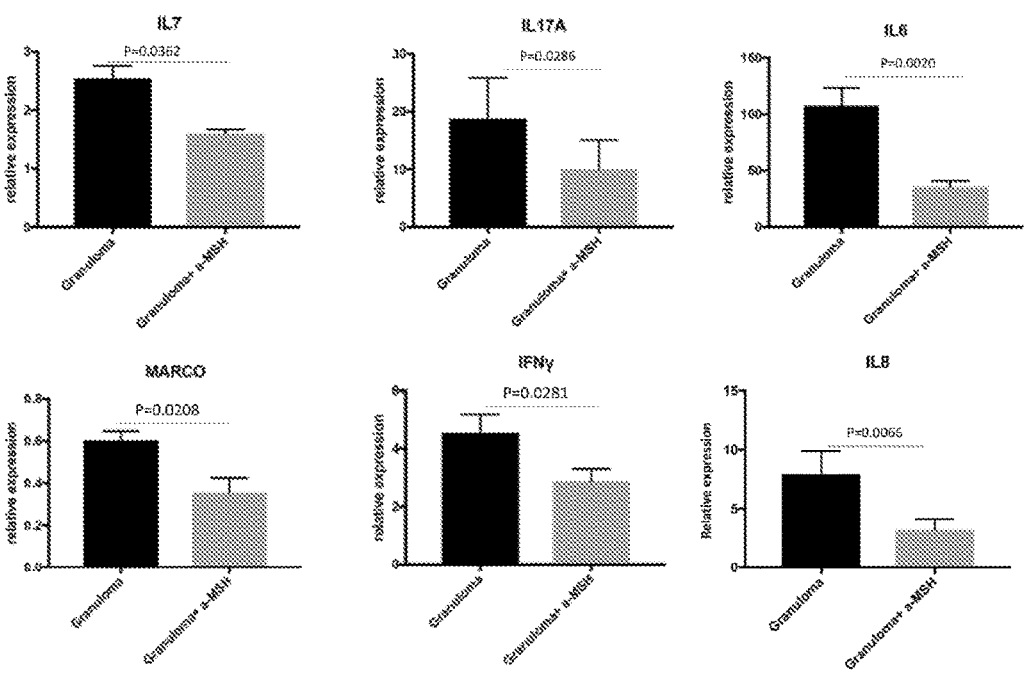
FIG. 12

C57Bl/6 mice, male, 8 weeks
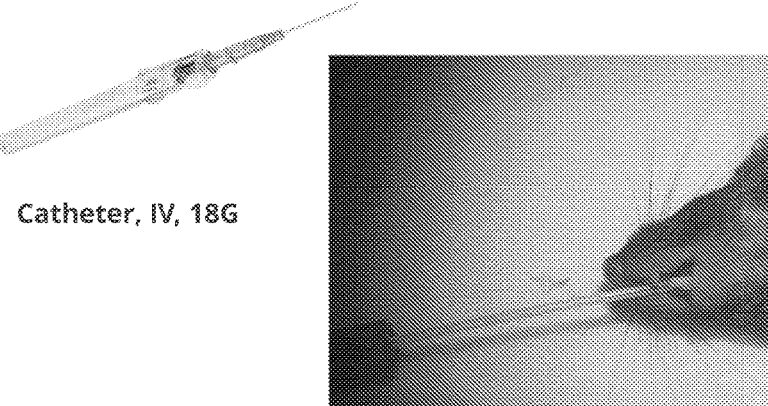
Catheter, IV, 18G
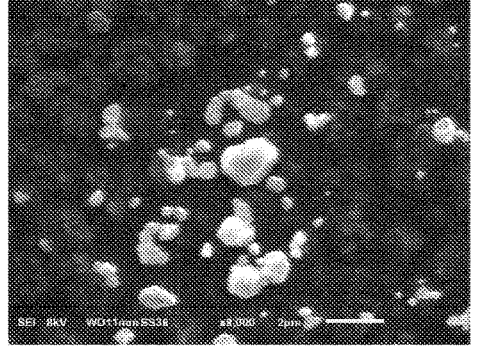
50 microL for first installation
20 microL for 3 more within 2 weeks
FIG. 18

SEQUENCE LISTING

```
<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: Synthetic construct

<400> SEQUENCE: 1

His Phe Arg Trp
1
```

METHODS OF PRODUCING GRANULOMAS AND ANIMAL MODELS OF SARCOIDOSIS

CROSS REFERENCE TO RELATED APPLICATIONS

This application claims the benefit of priority under 35 U.S.C. § 371 of International Application No. PCT/US2020/039761, filed Jun. 26, 2020, which claims the benefit of the filing date of U.S. Provisional Application No. 62/868,129, filed on Jun. 28, 2019. The content of these earlier filed applications is hereby incorporated by reference in its entirety.

REFERENCE TO A SEQUENCE LISTING

The Sequence Listing submitted herein as a text file named "37759_0232U2_Sequence_Listing.txt," created on Dec. 28, 2020, and having a size of 484 bytes is hereby incorporated by reference pursuant to 37 C.F.R. § 1.52(e)(5).

BACKGROUND

Sarcoidosis is a common condition in the U.S. population especially African-Americans with a prevalence of 39 in 100,000 and mostly affects adults aged 20-40 years old (Lazarus A. et al., *Dis Mon* 2009; 55: 649-660). Sarcoidosis related mortality is associated with pulmonary fibrosis (Nunes H, et al., *Orphanet J Rare Dis* 2007; 2: 46). In 2009-2010, there were 1315 sarcoidosis related deaths with an age-adjusted rate of 0.234 per 100,000 year-persons (http://wonder.cdc.gov/ucd-icd10.html Jul. 17, 2013). African Americans have 17 times the mortality rate due to sarcoidosis compared to Caucasians (Iannuzzi M C, et al., *N Engl J Med* 2007; 357: 2153-2165).

The etiology of sarcoidosis remains unclear, however it is considered an airborne disease, at least in a subset of patients, since the lungs, eyes and skin are the most affected organs. The possible environmental etiologies include exposure to dusts, microbe-rich environments and chemical agents (Newman L S, et al., *American journal of respiratory and critical care medicine* 2004; 170: 1324-1330); and Kucera G P, et al., *Chest* 2003; 123: 1527-1535). Various microbial agents have been associated with sarcoidosis. Mycobacteria and propionibacteria are the most cited pathogens in sarcoidosis pathogenesis with the thought that an uncontrolled immune response to particular antigens leads to immunopathology (Dubaniewicz A, et al., *J Clin Microbiol* 2006; 44: 3448-3451; Chen E S, et al., *American journal of respiratory and critical care medicine* 2010; 181: 360-373; Oswald-Richter K A, et al., *Journal of clinical immunology* 2012; 32: 1129-1140; Fang C, et al., *PloS one* 2016; 11: e0154716; Brownell I, et al., *American journal of respiratory cell and molecular biology* 2011; 45: 899-905; Brownell I, et al., *American journal of respiratory cell and molecular biology* 2011; 45: 899-905; and Rutherford R M, et al., *Chest* 2004; 125: 354).

SUMMARY

Disclosed herein are animals comprising one or more granulomas, wherein the one or more granulomas comprise *Mycobacterium abscessus* cell wall microparticles.

Disclosed herein are animals comprising one or more granulomas, wherein the one or more granulomas are produced by injection of one or more of a *Mycobacterium abscessus* cell wall microparticle.

Disclosed herein are methods of inducing sarcoidosis in an animal, the methods comprising administering one or more *Mycobacterium abscessus* cell wall microparticles to the animal.

Disclosed herein are methods of producing an in vitro granuloma, the methods comprising: (a) isolating one or more cell wall microparticles from one or more *Mycobacterium abscessus* strains; and (b) culturing the one or more of the isolated cell wall microparticles from step (a) with one or more peripheral blood mononuclear cells, thereby producing an in vitro granuloma.

Disclosed herein are methods of producing a *Mycobacterium abscessus* cell wall microparticle, the method comprising: (a) lysing cells obtained from a rough colony of one or more strains of *Mycobacterium abscessus*, wherein the lysis buffer comprises a protease inhibitor and a detergent; (b) centrifuging the cells from (a) so as to produce a pellet and a supernatant liquid; and collecting the supernatant; (c) centrifuging the supernatant so as to produce a second pellet and a second supernatant liquid; and collecting the second pellet; and (d) contacting the second pellet with a lysis buffer and heating to a temperature of at least 90° C., wherein the lysis buffer comprises a protease inhibitor and a detergent; thereby forming *Mycobacterium abscessus* cell wall microparticles.

Disclosed herein are methods of producing a *Mycobacterium abscessus* cell wall microparticle, the method comprising: (a) obtaining cells from a rough colony of one or more strains of *Mycobacterium abscessus*; (b) lysing the cells in a lysis buffer, wherein the lysis buffer comprises a protease inhibitor and a detergent; (c) centrifuging the cells from (b) so as to produce a pellet and a supernatant liquid; and collecting the supernatant; (d) centrifuging the supernatant so as to produce a second pellet and a second supernatant liquid; and collecting the second pellet; and (e) contacting the second pellet with a lysis buffer and heating to a temperature of at least 90° C., wherein the lysis buffer comprises a protease inhibitor and a detergent; thereby forming *Mycobacterium abscessus* cell wall microparticles.

Other features and advantages of the present compositions and methods are illustrated in the description below, the drawings, and the claims.

BRIEF DESCRIPTION OF THE DRAWINGS

FIGS. 1A-D show SEM images from microparticles from MAB. FIGS. 1A, 1B, and 1C show clusters of particles with a scale bar of 1, 2, and 5 μm respectively. FIG. 1D shows surface area of particles ranging from <1 μm to 9 μm.

FIG. 2A shows SEM images of a granuloma with clusters of macrophages and lymphocytes around it. FIG. 2B shows a granuloma in the center with a few smaller granulomas around it with a background of PBMCs taken with a low power field microscope (×20). FIG. 2C shows an image of a granuloma with high power field (60×) with a size more than 100 nm. FIG. 2D shows immunofluorescence images from a mature granuloma developed in vitro from PBMC of subjects with sarcoidosis. Top row shows CD4 positive cells, middle row shows CD8 positive cells, and bottom row shows PD-L1 positive cells. PD-L1 shows activation of probable T cells and macrophages. The left images are DAPI staining, middle immunofluorescence for antibodies, the right images overlapped.

FIG. 6A shows secretion of Th1 cytokines (IL-2R, IL7, IL-12, and IFN-gamma), and macrophage related cytokines (CCL2, CCL3, CCL4, CXCL9). FIG. 6B shows secretion of other cytokines (TNF-alpha, GM-CSF, IL-6, IL-10, CCL5 and CXCL10).

FIG. 7A shows IL-2R, IL6, IL-7, IL-10, IL-12, IL-15, GM-CSF, and IFN-gamma. FIG. 7B shows CCL2, CCL3, CCL4, CCL5, CCL11, CXCL9 and CXCL10.

FIG. 11 shows pathway analysis of RNASeq from a granuloma developed from PBMC of sarcoidosis subjects treated with α-MSH vs. a granuloma of the same patients treated with saline. DAVID version 6.8 was used to perform analysis. The results show treatment with α-MSH activates pathways related to immune system process including tolerance induction. (Corrected P value (FDR)<0.05, and Fold Change 2.5).

FIG. 12 shows gene expression profiles of a developed granuloma from PBMC of subjects with sarcoidosis and treated with α-MSH.

FIG. 18 shows the steps of establishing a lung sarcoidosis model.

DETAILED DESCRIPTION

Figures 2A, 2B, 2C, 2D, 3:
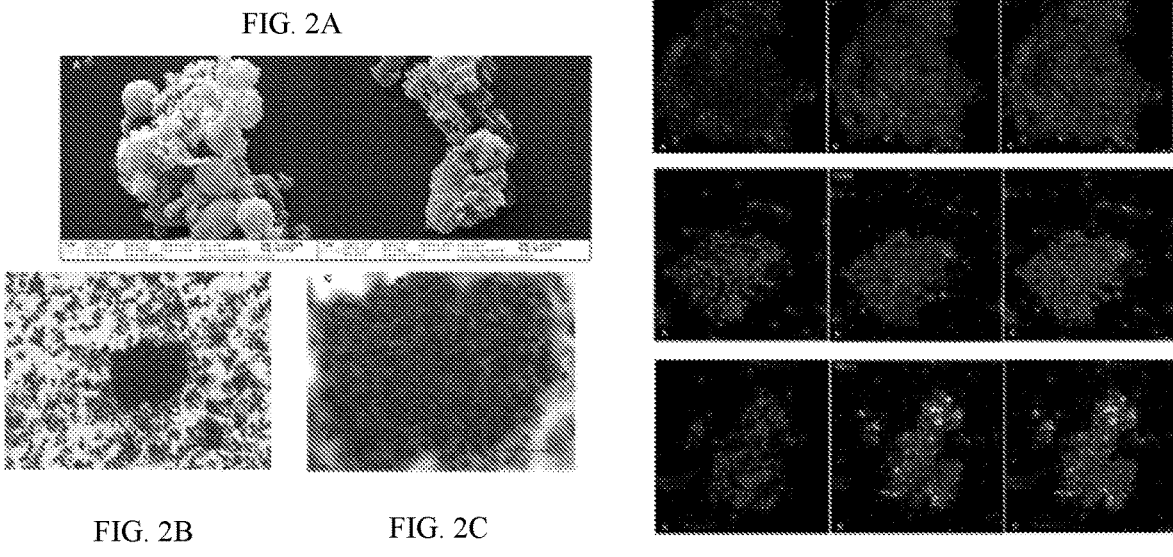
FIGS. 2A-D shows developed in vitro granuloma from PBMC of subjects with sarcoidosis.
FIG. 3 shows the analysis of RNASeq from granuloma developed from PBMC of sarcoidosis subjects treated with microparticles vs. PBMC of the same patients treated with saline. The results show that developed granuloma overexpressed several immune genes including IL8, IL6, TNF-α, IL-17a, IFN-gamma, CCL7 and CSF3. (Corrected P value (FDR) <0.01, and Fold Change 2.5). CSF3: Colony Stimulating Factor 3, CXCL1: C-X-C Motif Chemokine Ligand 1, CXCL2: C-X-C Motif Chemokine Ligand 2, CXCL3: C-X-C Motif Chemokine Ligand 3, CXCL5: C-X-C Motif Chemokine Ligand 5, CXCL6: C-X-C Motif Chemokine Ligand 6, IL1B: Interleukin 1 Beta, IL6: Interleukin 6, IL8: Interleukin 8, MMPI: Matrix Metallopeptidase 1, MMP3: Matrix Metallopeptidase 3, NFKBIA: NFKB Inhibitor Alpha, PTGS2: Prostaglandin-Endoperoxide Synthase 2, CCL7: Chemokine (C-C motif) ligand 7, CCL20: Chemokine (C-C motif) ligand 20, TNF: Tumor necrosis factor family, TNFAIP2: TNF Alpha Induced Protein 2, MAPK12: Mitogen-Activated Protein Kinase 12, CCL17: CCL7: Chemokine (C-C motif) ligand 17, CSF2: Colony Stimulating Factor 2, IL-17A: Interleukin 17A, IFNG: Interferon gamma.

The present disclosure can be understood more readily by reference to the following detailed description of the invention, the figures and the examples included herein.

Before the present compositions and methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

Moreover, it is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including matters of logic with respect to arrangement of steps or operational flow, plain meaning derived from grammatical organization or punctuation, and the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

Definitions

As used in the specification and the appended claims, the singular forms "a," "an" and "the" include plural referents unless the context clearly dictates otherwise.

The word "or" as used herein means any one member of a particular list and also includes any combination of members of that list.

Throughout the description and claims of this specification, the word "comprise" and variations of the word, such as "comprising" and "comprises," means "including but not limited to," and is not intended to exclude, for example, other additives, components, integers or steps. In particular, in methods stated as comprising one or more steps or operations it is specifically contemplated that each step comprises what is listed (unless that step includes a limiting term such as "consisting of"), meaning that each step is not intended to exclude, for example, other additives, components, integers or steps that are not listed in the step.

Ranges can be expressed herein as from "about" or "approximately" one particular value, and/or to "about" or "approximately" another particular value. When such a range is expressed, a further aspect includes from the one particular value and/or to the other particular value. Similarly, when values are expressed as approximations, by use of the antecedent "about," or "approximately," it will be understood that the particular value forms a further aspect. It will be further understood that the endpoints of each of the ranges are significant both in relation to the other endpoint and independently of the other endpoint. It is also understood that there are a number of values disclosed herein and that each value is also herein disclosed as "about" that particular value in addition to the value itself. For example, if the value "10" is disclosed, then "about 10" is also disclosed. It is also understood that each unit between two particular units is also disclosed. For example, if 10 and 15 are disclosed, then 11, 12, 13, and 14 are also disclosed.

As used herein, the terms "optional" or "optionally" mean that the subsequently described event or circumstance may or may not occur and that the description includes instances where said event or circumstance occurs and instances where it does not.

As used herein, the term "subject" refers to the target of administration, e.g., a human. Thus, the subject of the disclosed methods can be a vertebrate, such as a mammal, a fish, a bird, a reptile, or an amphibian. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.). In one aspect, a subject is a mammal. In another aspect, the subject is a human. The term does not denote a particular age or sex. Thus, adult, child, adolescent and newborn subjects, as well as fetuses, whether male or female, are intended to be covered.

As used herein, the term "patient" refers to a subject afflicted with a disease or disorder or condition. The term "patient" includes human and veterinary subjects. In some aspects of the disclosed methods, the "patient" has been diagnosed with a need for treatment for healing of bone injuries, such as, for example, prior to the administering step.

As used herein, the term "treating" refers to partially or completely alleviating, ameliorating, relieving, delaying onset of, inhibiting or slowing progression of, reducing severity of, and/or reducing incidence of one or more symptoms or features of a particular disease, disorder, and/or condition. Treatment can be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition. For example, the disease, disorder, and/or condition can be sarcoidosis.

Sarcoidosis is a multi-organ granulomatous disease of unknown etiology that is associated with significant morbidity and mortality in the U.S. and affects hundreds of thousands of people around the world (Mirsaeidi M, et al., *Chest* 2015; 147: 438-449). Although the etiology of this condition is not well-known, there are significant similarities between sarcoidosis and other granuloma-forming diseases including mycobacterial, other microbial infections and environmental agents (Chen E S, et al., *Clinics in chest medicine* 2008; 29: 365-377). In the affected organ, sarcoidosis triggers elicit an early inflammatory reaction characterized by cellular recruitment of TH1 helper cells and in the later phase macrophages play an important role that leads to granuloma formation. In certain patients, anti-inflammatory responses, including cytokines and apoptosis, are activated to facilitate tissue healing and repair (Koh T J, et al., *Expert Rev Mol Med* 2011; 13: e23). This process is an important step in defining the clinical outcome of sarcoidosis. Almost 50% of sarcoidosis patients require systemic steroid therapy. In up to 20% of patients, the inflammatory process continues despite steroids and leads to tissue remodeling with fibrosis (Patterson K C, et al., *Annals of the American Thoracic Society* 2013; 10: 362-370).

A major limitation in sarcoidosis research is the lack of an appropriate experimental animal model to mimic disease. The etiology and pathogenesis of sarcoidosis is poorly understood and that limits effective modeling. However, the association of sarcoidosis with viral and bacterial antigens is well documented. *Propionibacterium acnes* and mycobacterial proteins are the most common antigens isolated from sarcoidosis lesions of the lung (Hajizadeh R, et al., Journal of clinical immunology 2007; 27: 445-454); Drake W P, et al., Infection and immunity 2007; 75: 527-530; Ichikawa H, et al., *World Association of Sarcoidosis and Other Granulomatous Disorders* 2008; 25: 15-20; and Eishi Y, et al., *J Clin Microbiol* 2002; 40: 198-204) and antigen-specific immune responses to mycobacterial virulence factors were found in bronchoalveolar lavage (BAL) samples from sarcoid patients (Oswald-Richter K A, et al., *Infection and immunity* 2009; 77: 3740-3748). Disclosed herein are animal models for sarcoidosis.

Animal Model of Sarcoidosis

The etiology and pathogenesis of sarcoidosis and the identification of diagnostic and therapeutic targets is limited by a lack of an appropriate animal model. This has resulted in limited pharmaceutical interest in development of new medicines for sarcoidosis. Development of an appropriate animal model is important to fill the knowledge gap in sarcoidosis and the greater the similarity to humans the model is, the better the translatability of experimental finding is to human disease. Recently, a few sarcoidosis models have been developed. Although the prior models were mouse or rat models, different antigens were used to develop sarcoidosis-like granulomas. Chen et al. (2010) used intraperitoneal injections of *M. tuberculosis* (MTB) protein (KatG) to Lewis rats or C57BL/6 mice and showed granuloma formation (Chen E S, et al., *American journal of respiratory and critical care medicine* 2010; 181: 360-373). A year later, Swaisgood et al. used another mycobacterial protein (superoxide dismutase A) to develop granulomas in mice (Swaisgood C M, et al., *American journal of respiratory cell and molecular biology* 2011; 44: 166-174). *Propionibacterium acnes* was used by 4 different research groups to develop mice sarcoidosis model in the last 10 years (Minami J, et al., *J Med Dent Sci* 2003; 50: 265-274; Kishi J, et al., *The European respiratory journal* 2011; 38: 415-424; Nishiwaki T, et al., *The American journal of pathology* 2004; 165: 631-639; and Werner J L, et al., *American journal of respiratory cell and molecular biology* 2016). Hemdon and co-workers developed a sarcoidosis rat model with challenging them with beads coated with *Helicobacter pylori* protein (Herndon B, et al., *J Comp Pathol* 2013; 148: 266-277). Huizar et al. administered multiwall carbon nanotubes oropharyngeally and showed granuloma formation (Huizar I, et al., *Respiratory research* 2013; 14: 7). The last model was developed by Samokhin et al. (2010) by using a knockout mouse for the apolipoprotein E gene and fed them with a high fat diet for 16 weeks to produce granulomas (Samokhin A O, et al., *Am J Pathol* 2010; 176: 1148-1156). The problem with these aforementioned models is there have been difficulty with reproducibility of clinical sarcoidosis. These models focused on granuloma formation and immune cell composition while neglecting the development of lymphadenopathy and the fatal aspect of sarcoidosis presentations, pulmonary fibrosis. The disclosed animal models overcome the difficulty with reproducibility and improve on the failures of the prior models.

Animal Model

Disclosed herein are animal models of sarcoidosis. In some aspects, the animal obtained by any of the methods described herein can be used as a model of sarcoidosis. Disclosed herein are lung sarcoidosis animal models. In some aspects, the animal obtained by any of the methods described herein can be used as a model of lung sarcoidosis. Disclosed herein are animals comprising one or more granulomas. In some aspects, the one or more granulomas can comprise one or more *Mycobacterium abscessus* cell wall microparticles. In some aspects, the one or more granulomas can be produced by injection or delivery of one or more of a *Mycobacterium abscessus* cell wall microparticle to the animal. Disclosed herein are animals comprising one or more granulomas, wherein the one or more granulomas comprise *Mycobacterium abscessus* cell wall microparticles. Disclosed herein are animals comprising one or more granulomas, wherein the one or more granulomas are produced by injection or delivery of one or more of a *Mycobacterium abscessus* cell wall microparticle to the animal In some aspects, microparticles (e.g. *Mycobacterium abscessus* cell wall microparticles) can be formulated in any suitable vehicle for delivery. In some aspects, one or more of the microparticles can be less than a sub-micron to 2 μm in size. In some aspects, the microparticles disclosed herein are MAB cell wall microparticles. For example, the microparticles can be placed into a pharmaceutically acceptable suspension, solution or emulsion. Suitable mediums include saline and liposomal preparations. More specifically, pharmaceutically acceptable carriers may include sterile aqueous of non-aqueous solutions, suspensions, and emulsions. Examples of non-aqueous solvents include but are not limited to propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media.

In some aspects, the one or more granulomas can form an aggregate. For example, disclosed herein are aggregates comprising granulomas produced from two or more types of Mycobacteria colonies disclosed herein. In some aspects, two types of Mycobacteria colonies (e.g., smooth and rough) can be cultured in solid media. Rough colonies usually develop into pathogen mycobacteria, particularly those that isolated from patients. In some aspects, the microparticles disclosed herein can be developed from rough colonies. In some aspects, the microparticles disclosed herein can be developed from a mixture of rough and smooth colonies.

In some aspects, the one or more granulomas (e.g., granulomas comprising one or more *Mycobacterium abscessus* cell wall microparticles) can be present in a lung of the animal. In some aspects, the one or more granulomas can be present in both lungs of the animal. In some aspects, the animal can exhibit a presentation of sarcoidosis or one or more symptoms of sarcoidosis compared to an animal without one or more granulomas present in the lung. In some aspects, the phenotype of the animal with one or more granulomas present in a lung can include but not limited to a non-necrotizing granuloma that differentiates it from mycobacterial or fungal granulomas. In some aspects, the one or more sarcoidosis symptoms (or presentation of sarcoidosis) can be pulmonary fibrosis or lymphadenopathy or splenomegaly. In some aspects, the one or more sarcoidosis symptoms (or presentation of sarcoidosis) can be weight loss compared to an animal without one or more granulomas present in the lung.

In some aspects, the lung of the disclosed animal models can be positive for one or more biomarkers. In some aspects, the lung of the disclosed animal models can be CD68+, CD4+, PD-L1+, PD-1+, CD45+ or a combination thereof. CD68 is a macrophage marker. CD4 is a lymphocyte marker. PD-L1 is a marker of activated T cells and B cells. PD-1 is a marker of T cells and pro-B cells. CD45 is a general lymphocyte marker.

In some aspects, the *Mycobacterium abscessus* cell wall microparticles can be derived from one or more strains of *Mycobacterium abscessus*. In some aspects, the one or more strains of *Mycobacterium abscessus* can exhibit a rough morphotype. In some aspects, the one or more strains of *Mycobacterium abscessus* can be *Mycobacterium abscessus* subspecies *abscessus*, or/and *Mycobacterium abscessus* subspecies *massiliense*.

In some aspects, the animal obtained by any of the methods disclosed herein can be of any species. In some aspects, the animal can be a mammal. In some aspects, the animal can be a rodent or a non-human primate. In some aspects, the animal can be a mouse. In some aspects, the animal can be a rat. Typically, the animal obtained by the method disclosed herein is not a human. In some aspects, the animal can also be a genetically modified animal, such as a "knockout" animal in which the function or expression of a gene has been reduced or eliminated.

Disclosed herein are animals having sarcoidosis obtained by or produced by any of the methods disclosed herein or with any of the disclosed compositions disclosed herein. In some aspects, the animal having sarcoidosis can be used as a model of sarcoidosis.

Methods

Disclosed herein are methods of making an animal comprising one or more granulomas, wherein the one or more granulomas comprise *Mycobacterium abscessus* cell wall microparticles. Disclosed herein are methods of making an animal comprising one or more granulomas, wherein the one or more granulomas are produced by injection or delivery of one or more of a *Mycobacterium abscessus* cell wall microparticle to the animal.

Disclosed herein are methods of inducing sarcoidosis in an animal. Disclosed herein are methods of inducing sarcoidosis in an animal. In some aspects, the methods can comprise administering one or more *Mycobacterium abscessus* cell wall microparticles to the animal. In some aspects, one or more *Mycobacterium abscessus* cell wall microparticles can be administered intratracheally or intranasally. In some aspects, the intratracheal or intranasal administration of one or more of the *Mycobacterium abscessus* cell wall microparticles can produce one or more lung granulomas. In some aspects, the one or more lung granulomas can form an aggregate. In some aspects, the aggregate can comprise one or more cellular markers. In some aspects, the granulomas described herein can comprise one or more cellular markers. In some aspects, the one or more cellular markers can be CD45+, CD68+, CD4+, PD-L1+, PD-1+, or a combination thereof.

In some aspects, the granuloma produced by one or more of the *Mycobacterium abscessus* cell wall microparticles can express one or more of the following cytokines or chemokines (and the genes that encode the proteins) can be increased: IL-1β, IL2R, IL6, IL7, IL-8, IL-10, IL12, IL-15, IFN-α, INF-γ, TNF-α, GM-CSF, CCL2, CCL3, CCL4, CCL5, and CXCL9. In some aspects, the granuloma produced by one or more of the *Mycobacterium abscessus* cell wall microparticles can express one or more of the following cytokines or chemokines (and the genes that encode the proteins) can be increased: IL-1β, IL2R, IL6, IL7, IL-8, IL-10, IL12, IL-15, IFN-α, INF-γ, TNF-α, GM-CSF, CCL2, CCL3, CCL4, CCL5, and CXCL9 as compared to a granulomas produced by other methods in the art. In some aspects, the granuloma produced by one or more of the *Mycobacterium abscessus* cell wall microparticles can express one or more of the following cytokines or chemokines (and the genes that encode the proteins) can be increased: IL36α, IL36β, IL36γ, IL23, IL1RL1, IL1RN, CCL5, CXCL11, CCL22, and CXCL10. In some aspects, the granuloma produced by one or more of the *Mycobacterium abscessus* cell wall microparticles can express one or more of the following cytokines or chemokines (and the genes that encode the proteins) can be increased: IL36a, IL36β, IL36γ, IL23, IL1RL1, IL1RN, CCL5, CXCL11, CCL22, and CXCL10 as compared to a granuloma produced by other methods in the art.

In some aspects, the granuloma produced by one or more of the *Mycobacterium abscessus* cell wall microparticles can express one or more of the following cytokines or chemokines (and the genes that encode the proteins) can be increased: IL-1β, IL2R, IL6, IL7, IL-8, IL-10, IL12, IL-15, IFN-α, INF-γ, TNF-α, GM-CSF, CCL2, CCL3, CCL4, CCL5, and CXCL9, CCL11, CCL22 (FC 2.8), CXCL10 (FC 2.5), IL36β (FC 41.3), IL36a (FC 18.4), IL36γ (FC 3.2), IL23A (FC 3.2), IL1RL1 (FC 3.1), IL1RN (FC 3.1), IL1RN (FC 2.6), MMP9 (FC 4, MX1, OSA1, ISG15, IL17a and IL-17f.

In some aspects, the granuloma produced by one or more of the *Mycobacterium abscessus* cell wall microparticles can express increased levels (or amounts) of inducible nitric oxide synthase and nitrotyrosine. In some aspects, the granuloma produced by one or more of the *Mycobacterium abscessus* cell wall microparticles can express increased levels (or amounts) of inducible nitric oxide synthase and nitrotyrosine as compared to a granuloma produced by other methods in the art.

In some aspects, the animal can exhibit one or more symptoms of sarcoidosis or a presentation of sarcoidosis. In some aspects, the one or more symptoms of sarcoidosis or presentation of sarcoidosis can be pulmonary nodules, fibrosis, splenomegaly, and/or lymphadenopathy.

Disclosed herein are methods of producing an in vitro granuloma. Disclosed herein are methods of producing an in vitro granuloma comprising: (a) isolating one or more cell wall microparticles from one or more *Mycobacterium abscessus* strains; and (b) culturing the one or more of the isolated cell wall microparticles from step (a) with one or more peripheral blood mononuclear cells, thereby producing an in vitro granuloma. In some aspects, the one or more peripheral blood mononuclear cells can be isolated from a treatment-naïve sarcoidosis patient. In some aspects, the granuloma can be produced in 1-4 days. In some aspects, the granuloma can comprise at least one macrophage or at least one lymphocyte. In some aspects, the one or more strains of *Mycobacterium abscessus* can exhibit a rough morphotype. In some aspects, the one or more strains of *Mycobacterium abscessus* can be *Mycobacterium abscessus* subspecies *abscessus*, or/and *Mycobacterium abscessus* subspecies *massiliense*.

Disclosed herein are methods of screening a compound for therapeutic use in the treatment of sarcoidosis. Disclosed herein are methods of screening a compound for therapeutic use in the treatment of sarcoidosis using an animal comprising one or more granulomas, wherein the one or more granulomas comprise *Mycobacterium abscessus* cell wall microparticles. Disclosed herein are methods of screening a compound for therapeutic use in the treatment of sarcoidosis using an animal comprising one or more granulomas, wherein the one or more granulomas are produced by injection or delivery of one or more of a *Mycobacterium abscessus* cell wall microparticle to the animal.

Disclosed herein are methods of screening a compound for therapeutic use in the treatment of sarcoidosis using any of the animal models or animals described herein. In some aspects, the animal can be used for assessing potential side effects of treatment of sarcoidosis. In some aspects, the compound can be for example, administered in a therapeutically effective amount to act to reduce one or more cytokines, downregulate one or more cytokine genes, reduce lung tissue inflammation or a combination thereof. In some aspects, the screening steps can include, for example, administering a compound to be screened to the animal described herein, waiting for a certain period of time, optionally repeating the administration, measuring levels of one or more cytokine(s), expression levels of cytokine genes, scoring the degree of lung tissue inflammation or a combination thereof, and selecting the compound according to its effect on the level of cytokine(s), expression levels of cytokine genes, the score of lung tissue inflammation. For example, if a compound tested allows a decrease in the score of lung tissue inflammation, it could be selected as a potential therapeutic drug against sarcoidosis. In some aspects, the method can provide an animal model as described herein, wherein the animal comprises one or more granulomas and administering the agent to the animal model. It then can be determined whether the agent is capable of delaying, for example, the onset of a sarcoidosis-related symptom in the animal model treating with the agent compared to the untreated animal model. In some aspects, it may be desirable to examine either singly or a set of symptoms as disclosed herein.

Alternatively, the animal disclosed herein can also be used for studying the mechanism of sarcoidosis, lung sarcoidosis, and/or one or more sarcoidosis-related symptoms. In some aspects, the use of an animal having sarcoidosis for studying the mechanism of the disease can be obtained by any of the methods disclosed herein. For instance, such an animal can be useful for understanding the physio-pathology or the molecular mechanism involved in sarcoidosis, lung sarcoidosis, and/or one or more sarcoidosis-related symptoms. In some aspects, the disclosed animal can be used to study changes in gut microbiota. In some aspects, the disclosed animal can have a reduction in the population of bifidobacteria, for example, in fecal and/or cecum samples. In some aspects, the disclosed animal can be used to study the role of nitric oxide signaling and its role in the inflammatory response in sarcoidosis.

Disclosed herein are methods of screening for a therapeutic agent for reducing or delaying the onset of a sarcoidosis-related symptom. Disclosed herein are methods of screening for a therapeutic agent for reducing or delaying the onset of a sarcoidosis-related symptom comprising: (a) providing an animal comprising one or more granulomas, wherein the one or more granulomas comprise *Mycobacterium abscessus* cell wall microparticles, wherein the mouse exhibits sarcoidosis-related symptoms; (b) administering the agent to the animal; and (c) determining whether the agent is capable of reducing or delaying the onset of sarcoidosis-related symptoms in the animal treated with the agent compared to an untreated animal model.

Disclosed herein are methods of screening for a therapeutic agent for reducing or delaying the onset of a sarcoidosis-related symptom comprising: (a) providing an animal comprising one or more granulomas, wherein the animal comprises one or more granulomas, wherein the one or more granulomas are produced by injection or delivery of one or more of a *Mycobacterium abscessus* cell wall microparticle to the animal, wherein the mouse exhibits sarcoidosis-related symptoms; (b) administering the agent to the animal; and (c) determining whether the agent is capable of reducing or delaying the onset of sarcoidosis-related symptoms in the animal treated with the agent compared to an untreated animal model.

In some aspects, the step of determining whether the agent is capable of reducing or delaying the onset of sarcoidosis-related symptoms in the animal treated with the agent can be compared to an animal disclosed herein treated with a vehicle. In some aspects, the sarcoidosis-related symptom can be one or more of reducing the production of one or more cytokines, downregulating one or more cytokine genes, reducing a lung tissue inflammation score or a combination thereof.

Disclosed herein are methods of screening for a therapeutic agent for reducing or delaying the onset of a sarcoidosis-related symptom. Disclosed herein are methods of screening for a therapeutic agent for reducing or delaying the onset of a sarcoidosis-related symptom comprising: (a) providing an animal comprising one or more granulomas, wherein the one or more granulomas comprise *Mycobacterium abscessus* cell wall microparticles, wherein the mouse exhibits sarcoidosis-related symptoms; (b) administering the agent to the animal; and (c) determining whether the agent is capable of reducing or delaying the onset of sarcoidosis-related symptoms in the animal treated with the agent compared to an untreated animal model, wherein the step of determining whether the agent is capable of reducing or delaying the onset of sarcoidosis-related symptoms in the animal treated with the agent is determined by comparing the animal to an animal disclosed herein treated with a vehicle. In some aspects, the step of determining whether the agent is capable of reducing or delaying the onset of sarcoidosis-related symptoms in the animal treated with the agent is determined by determining the ability of the agent to reduce the production of one or more cytokines, to downregulate one or more cytokine genes, to reduce a lung tissue inflammation score or a combination thereof.

Disclosed herein are methods of screening for a therapeutic agent for reducing or delaying the onset of a sarcoidosis-related symptom comprising: (a) providing an animal comprising one or more granulomas, wherein the animal comprises one or more granulomas, wherein the one or more granulomas are produced by injection or delivery of one or more of a *Mycobacterium abscessus* cell wall microparticle to the animal, wherein the mouse exhibits sarcoidosis-related symptoms; (b) administering the agent to the animal; and (c) determining whether the agent is capable of reducing or delaying the onset of sarcoidosis-related symptoms in the animal treated with the agent compared to an untreated animal model, wherein the step of determining whether the agent is capable of reducing or delaying the onset of sarcoidosis-related symptoms in the animal treated with the agent is determined by comparing the animal to an animal disclosed herein treated with a vehicle. In some aspects, the step of determining whether the agent is capable of reducing or delaying the onset of sarcoidosis-related symptoms in the animal treated with the agent is determined by determining the ability of the agent to reduce the production of one or more cytokines, to downregulate one or more cytokine genes, to reduce a lung tissue inflammation score or a combination thereof.

In some aspects, the cytokine that can be reduced are Th1 cytokines. In some aspects, Th1 cytokines can be reduced in bronchoalveolar isolated single cells. In some aspects, Th1 cytokines can be reduced in lung isolated single cells. In some aspects, the sarcoidosis-related symptoms can be elevated cytokines, elevated chemokines, elevated cytokine genes, lung tissue inflammation or a combination thereof. Cytokines are a family of small proteins that are important in cell signaling. In some aspects, cytokines can include interleukins, lymphokines, monokines, interferons, colony stimulated factors, and chemokines. Chemokines are a family of cytokines that recruit or attract white blood cells (e.g., leukocytes). In some aspects, the step of determining whether the agent is capable of reducing or delaying the onset of sarcoidosis-related symptoms in the animal treated with the agent comprises determining whether one or more of the following cytokines or chemokines (and the genes that encode the proteins) are reduced upon exposure to the agent: IL2R, IL7, IL12, INF-γ, CCL2, CCL3, CCL4, TNF-α, and IL-6. In some aspects, the step of determining whether the agent is capable of reducing or delaying the onset of sarcoidosis-related symptoms in the animal treated with the agent comprises determining whether one or more of the following cytokines or chemokines (and the genes that encode the proteins) is reduced: IL-1β, IL-2R, IL-6, IL-7, IL-8, IL-10, IL-12, IL-15, IFN-α, IFN-γ, TNF-α, GM-CSF, CCL2, CCL3, CCL4, CCL5, CXCL9 and CCL11. In some aspects, the step of determining whether the agent is capable of reducing or delaying the onset of sarcoidosis-related symptoms in the animal treated with the agent comprises determining whether one or more of the following cytokines or chemokines (and the genes that encode the proteins) is reduced: IL-6, IL-7, IL-2R, CCL2, CCL3, CCL4, CXCL9, and CXCL10, but, less IL-12, CCL5 and IFN-γ. In some aspects, the step of determining whether the agent is capable of reducing or delaying the onset of sarcoidosis-related symptoms in the animal treated with the agent comprises determining whether one or more of the following cytokines or chemokines (and the genes that encode the proteins) is reduced: IL36β (FC 41.3), IL36α (FC 18.4), IL36γ (FC 3.2), IL23A (FC 3.2), IL1RL1 (FC 3.1), IL1RN (FC 3.1) and IL1RN (FC 2.6). In some aspects, the step of determining whether the agent is capable of reducing or delaying the onset of sarcoidosis-related symptoms in the animal treated with the agent comprises determining whether one or more of the following cytokines or chemokines (and the genes that encode the proteins) is reduced: CCL5 (FC 8.8), CXCL11 (FC 3.1), CCL22 (FC 2.8) and CXCL10 (FC 2.5). In some aspects, the step of determining whether the agent is capable of reducing or delaying the onset of sarcoidosis-related symptoms in the animal treated with the agent comprises determining whether a matrix metallopeptidase (MMP) 9 (FC 4) is reduced. In some aspects, the step of determining whether the agent is capable of reducing or delaying the onset of sarcoidosis-related symptoms in the animal treated with the agent comprises determining whether one or more of the following proteins is reduced or downregulated: MX1, OSA1, ISG15 and IFN-α. In some aspects, the step of determining whether the agent is capable of reducing or delaying the onset of sarcoidosis-related symptoms in the animal treated with the agent comprises determining whether IL17a and IL-17f can be reduced or downregulated. In some aspects, the step of determining whether the agent is capable of reducing or delaying the onset of sarcoidosis-related symptoms in the animal treated with the agent comprises determining whether there is an improvement in lung inflammation. Lung inflammation score can be determined. Slides can be analyzed and scored for cellular inflammation under light microscopy. The lung inflammation score can be performed based on the following: three fields with the highest intensity of inflammatory infiltrates in each mouse at 100× power magnification can be identified, and each field can be assigned a percentage of the area that the inflammatory infiltrates occupied. The percentages can then be averaged for the 3 examining fields. For example, if the percentage of field one is 60%; the percentage of field two is 80%; and the percentage of field thee is 100%, the average can be calculated by adding 60+80+100 for the sum of 240, and then dividing the sum (240) by 3. Thus, the average or lung inflammation score would be 80% (240/3). Changes or improvements in lung inflammation can be determined by comparing the lung inflammation score after administration of a test compound using the animal model described herein to the lung inflammation score after administration of a vehicle compared to an untreated animal model. In some aspects, changes in the expression of one or more genes disclosed herein can be carried out using RNASeq or RT-PCR. In some aspects, changes in the expression or amount of one or more cytokines or chemokines disclosed herein can be carried out using ELISA or Western blot.

Disclosed herein are any of methods or compositions described herein wherein the animal can be a mouse.

Disclosed herein are methods of producing one or more microparticles. Disclosed herein are methods of producing one or more *Mycobacterium abscessus* cell wall microparticles.

Disclosed herein are methods of producing a *Mycobacterium abscessus* cell wall microparticle, the method comprising: (a) lysing cells obtained from a rough colony of one or more strains of *Mycobacterium abscessus*, wherein the lysis buffer comprises a protease inhibitor and a detergent; (b) centrifuging the cells in (a) so as to produce a pellet and a supernatant liquid; and collecting the supernatant; (c) centrifuging the supernatant so as to produce a second pellet and a second supernatant liquid; and collecting the second pellet; and (d) contacting the second pellet with a lysis buffer and heating to a temperature of at least 90° C., wherein the lysis buffer comprises a protease inhibitor and a detergent; thereby forming *Mycobacterium abscessus* cell wall microparticles.

Disclosed herein are methods of producing a *Mycobacterium abscessus* cell wall microparticle, the method comprising: (a) obtaining cells from a rough colony of one or more strains of *Mycobacterium abscessus*; (b) lysing the cells in a lysis buffer, wherein the lysis buffer comprises a protease inhibitor and a detergent; (c) centrifuging the cells in (b) so as to produce a pellet and a supernatant liquid; and collecting the supernatant; (d) centrifuging the supernatant so as to produce a second pellet and a second supernatant liquid; and collecting the second pellet; and (e) contacting the second pellet with a lysis buffer and heating to a temperature of at least 90° C., wherein the lysis buffer comprises a protease inhibitor and a detergent; thereby forming *Mycobacterium abscessus* cell wall microparticles.

In some aspects, the methods can further comprise isolating the *Mycobacterium abscessus* cell wall microparticles. In some aspects, the methods can further comprise adding cells from a smooth colony of one or more strains of *Mycobacterium abscessus* to the cells of step (a) prior to step (b). In some aspects, the methods can further comprise adding cells from a smooth colony of one or more strains of *Mycobacterium abscessus* to the cells from a rough colony of one or more strains of *Mycobacterium abscessus* prior to the lysing. In some aspects, cells in step (a) can be collected after having reached an optical density at 600 nm between 1.0 and 1.2 after before the lysing in step (b). In some aspects, cells obtained from a rough colony of one or more strains of *Mycobacterium abscessus* and/or cells obtained from a mixture of rough colony of one or more strains of *Mycobacterium abscessus* and a smooth colony of one or more strains of *Mycobacterium abscessus* can be collected after having reached an optical density at 600 nm between 1.0 and 1.2 before the lysing in step (b). In some aspects, the cells can be one or more cells. In some aspects, the cells obtained from a rough colony of one or more strains of *Mycobacterium abscessus* and/or cells obtained from a mixture of rough colony of one or more strains of *Mycobacterium abscessus* and a smooth colony of one or more strains of *Mycobacterium abscessus* can be mixed together and permitted to grow until reaching an optical density at 600 nm between 1.0 and 1.2.

Any number (e.g., 1, 2, 3, 4, 5, 6, 7, 8, etc.) of *Mycobacterium abscessus* strains can be used to make the microparticles. In some aspects, strains of *Mycobacterium abscessus* from a rough colony are used to make the *Mycobacterium abscessus* cell wall microparticle. In some aspects, strains of *Mycobacterium abscessus* from a rough colony can be combined with strains of *Mycobacterium abscessus* from a smooth colony to make the *Mycobacterium abscessus* cell wall microparticle. In some aspects, the ratio of strains of *Mycobacterium abscessus* from a rough colony to the strains of *Mycobacterium abscessus* from a smooth colony can be 2:1, 3:1, 4:1 or 5.1. In some aspects, more strains of *Mycobacterium abscessus* are from a rough colony than the strains of *Mycobacterium abscessus* from a smooth colony. In some aspects, the cells from a rough colony can be from a sample from a subject infected with *Mycobacterium abscessus*. In some aspects, the cells from a smooth colony can be from an environmental sample. In some aspects, the environmental sample can be from soil.

In some aspects, the exposure to a lysis buffer can be sufficient to produce a cell lysate. In some aspects, the lysis buffer can comprise a protease inhibitor and a detergent. Examples of protease inhibitors include, but are not limited to EDTA, Pepstatin A, and E-64. Examples of detergents include, but are not limited to Tween-20, sodium dodecyl sulfate, and Triton X-100. In some aspects, the exposure to a lysis buffer can comprise multiple treatments. In some aspects, the lysis buffer treatment can comprise two or more sequential lyses at intervals of between 5 minutes and 30 minutes. In some aspects, the methods described herein can comprise as step of removing one or more intact cell from a rough colony, a smooth colony or a combination thereof of one or more strains of *Mycobacterium abscessus*.

*M. abscessus* cell wall is a complex composition comprising mycolic acid. In some aspects, the *M. abscessus* cell wall can be structurally changed. In some aspects, the *M. abscessus* cell wall can be structurally changed by heating the *M. abscessus* cell or cell wall to at least 90° C. In some aspects, cells from one or more strains of *M. abscessus* can be heated at a temperature of at least 90° C. In some aspects, cells or cell walls from one or more strains of *M. abscessus* can be heated to a temperature of 95° C. In some aspects, cells or cell walls from one or more strains of *M. abscessus* can be further exposed to PBS with 0.1% sds, and 10 mM EDTA.

In some aspects, one or more of the microparticles can be less than a sub-micron to 2 μm in size. In some aspects, the microparticles disclosed herein can be MAB cell wall microparticles.

In some aspects, the *Mycobacterium abscessus* cell wall microparticles produced by the method described herein can form a granuloma. In some aspects, the granuloma can express one or more T helper cell markers. In some aspects, the one or more T helper cell markers are Th1, Th17 or a combination thereof. In some aspects, the granuloma can express a CD68 cell marker. In some aspects, the granuloma can express CD4+, CD68+, PD-L1 or a combination thereof.

Also disclosed herein are methods of isolating one or more *Mycobacterium abscessus* cell wall microparticles.

Also, disclosed herein are methods of treating persistent inflammation in a subject with sarcoidosis. In some aspects, the sarcoidosis can be pulmonary sarcoidosis. In some aspects, the subject can be identified in need of treatment before any administration of a therapeutic agent. In some aspects, the method can comprise administering to a subject a therapeutically effective amount of α-MSH. In some aspects, administration of α-MSH can reduce the amount or expression level of one or more of IL-7, IL7R, and IFN-γ and CCL3. In some aspects, the reduction of one or more of IL-7, IL7R, and IFN-γ and CCL3 can be via downregulation of MARCO (gene and protein). In some aspects, administration of α-MSH can induce the phosphorylation of CREB.

EXAMPLES

Example 1: α-Melanocyte Stimulating Hormone Anti-Inflammatory Properties Via p-CREB Inhibition in Sarcoidosis-Like Granuloma Model Abstract. Lung inflammation from sarcoidosis is characterized by a complex cascade of immunopathologic events, including leukocyte recruitment and granuloma formation. There are few medications available to clinicians to treat this condition. Corticosteroids are the cornerstone of most therapeutic approaches; however, the well-established side-effects associated with prolonged corticosteroid use make these agents undesirable for chronic disease management. α-melanocyte stimulating hormone (α-MSH) is a melanocortin signaling peptide with anti-inflammatory properties. Described herein are the effects of α-MSH in an in vitro sarcoidosis model.

Methods. An in vitro sarcoid-like granuloma model was developed by challenging PBMC derived from patients with confirmed treatment-naïve sarcoidosis with microparticles generated from *Mycobacterium abscessus* cell wall. Unchallenged PBMC, and developed granulomas, were treated daily with 10 μM of α-MSH or saline as control. Cytokine concentrations in culture supernatants were measured using Illumina multiplex Elisa and cell extracts by western blot. Gene expression were analyzed using RNA-Seq and RT-PCR. Protein secretion and gene expressions of IL-7, IL-7R, IFN-γ, MC1R, NFkB, and phosphorylated NFkB (p-NFkB), MARCO, and p-CREB were measured with western blot and RNAseq, respectively.

Results. A significant increase in IL-7, IL-7R, and IFN-γ protein expression was found in developed granulomas compared to microparticle unchallenged PBMC. Treatment with α-MSH significantly reduced IL-7, IL-7R, and IFN-γ granuloma protein expression compared with controls.

Compared with microparticle unchallenged PBMCs, total NFkB, and p-NFkB was significantly increased in developed granulomas and p-CREB was significantly down-expressed. Treatment with α-MSH promoted a significantly higher concentration of p-CREB in granulomas. The anti-inflammatory effects of α-MSH were blocked by specific p-CREP inhibition.

Conclusion. α-MSH has anti-inflammatory properties in this in vitro granuloma model, an effect mediated by induction of phosphorylation of CREB.

Introduction. Sarcoidosis is a multi-organ granulomatous disease of unknown etiology that affects thousands of people around the world and is associated with significant morbidity and mortality (Mirsaeidi M, et al., *Chest* 2015; 147: 438-449). In affected organs, sarcoidosis triggers an inflammatory reaction characterized by cellular recruitment of TH1 helper cells followed by macrophages that play an important role leading to granuloma formation (Chen E S, et al., *Nat Rev Rheumatol* 2011; 7: 457-467). The etiology and pathogenesis of sarcoidosis is poorly understood, which has limited the development of an effective in vitro sarcoidosis model. A strong association with bacterial antigens has been described, with mycobacterial proteins being the most common antigens isolated from sarcoid lesions of the lung (Hajizadeh R, et al., *Journal of clinical immunology* 2007; 27: 445-454); Drake W P, et al., *Infect Immun* 2007; 75: 527-530; Ichikawa H, et al., *Sarcoidosis Vasc Diffuse Lung Dis* 2008; 25: 15-20; and Eishi Y, et al., *Journal of clinical microbiology* 2002; 40: 198-204). In addition, antigen-specific immune responses to mycobacterial virulence factors have be detected in bronchoalveolar lavage fluid (BALF) from sarcoidosis patients (Oswald-Richter et al., *Infect Immun* 2009; 77: 3740-3748).

These data suggest that at least in some patients, sarcoidosis may occur from abnormal inflammation in response to mycobacterial antigens and that mycobacterial extracts are a suitable way to induce granulomas in vitro.

Approximately 50% of sarcoidosis patients require systemic steroid therapy. Despite this, up to 20% of treated patients continue to exhibit a persistent granulomatous inflammatory process with progression to tissue remodeling and fibrosis (Patterson K C, et al., *Annals of the American Thoracic Society* 2013; 10: 362-370). The US Food and Drug Administration (FDA) has approved two medications to treat this condition: prednisone and repository corticotropin injections (Acthar-Gel®) (Miller M A, et al., *Ann Intern Med* 1952; 37: 776-784; and Baughman R P, et al., *Respiratory medicine* 2016; 110: 66-72). The persistence of symptoms and the involvement of vital organs are factors that demand prolonged treatment courses, often associated with additional comorbidities. For this reason, alternative less toxic therapeutic agents with equal or higher efficacy is urgently needed. α-Melanocyte-stimulating hormone (α-MSH) is a 13 amino acid peptide produced by post-translational processing of the hormone proopiomelanocortin (POMC) (Catania A, et al., *Endocr Rev* 1993; 14: 564-576) that may have an effect in sarcoidosis-related inflammation as it has been shown to have anti-inflammatory properties in ocular and intestinal tissues (Colombo G, et al., *Neuroimmunomodulation* 2002; 10: 208-216; and Nishida T, et al., *International immunopharmacology* 2004; 4: 1059-1066).

The results show that exposure of human peripheral blood mononuclear cells (PBMCs) to microparticles generated from mycobacterial cell walls induces granuloma formation in vitro akin to the granulomatous inflammation observed in clinical sarcoidosis characterized by a TH1 and TH17 inflammatory response. In this model, the results show that α-MSH reduces inflammation via induction of CREB phosphorylation.

Results. Development of an in vitro granuloma model. Given the association between mycobacteria and sarcoidosis (Fang C, et al., *PLoS One* 2016; 11: e0154716; Brownell I, et al., *Am J Respir Cell Mol Biol* 2011; 45: 899-905 and Shamaei M P M, et al., *Sarcoidosis Vasculitis and Diffuse Lung Disease* 2018; 34 236-241) microparticles were developed from *Mycobacterium abscessus* (MAB) to stimulate T cells and monocytes from PBMC to develop granulomas. MAB cell wall microparticles were isolated using protocol described herein. For example, eight strains of MAB with a rough colony isolated and two strains isolated from environment (soil samples) was used and the particle size was characterized by analyzing high-quality scanning electron microscope (SEM) images. As shown in FIG. 1, the MAB cell wall particle size ranged from less than a sub-micron to 2 μm. To prove that the microparticles were bacteria free, they were cultured to confirm no growth before each experiment.

MAB particles <2 μm with an equivalent multiplicity of infection (MOI) of 10:1 (and a total endotoxin level of <1.115 EU/ml) were incubated with PMBCs extracted from treatment-naive individuals with sarcoidosis who had negative tuberculosis IFN-γ release assays (IGRA). After 72 h, H&E staining and scanning electron microcopy (SEM) of cultures revealed cellular structures consistent with matured granulomas (see FIG. 2). Granuloma features were confirmed by immunohistochemistry by showing positive stains for CD4$^+$, CD68$^+$ as well as PD-L1 as shown in FIG. 2.

Figure 4:
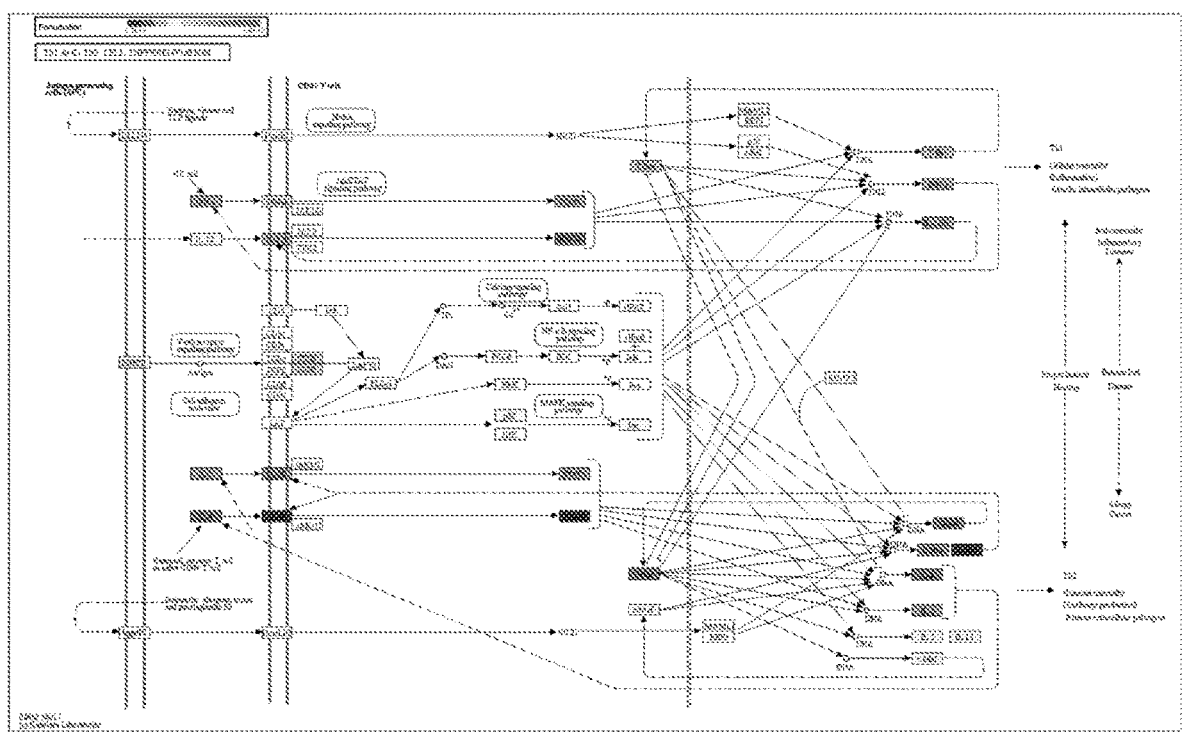
FIG. 4 shows the pathway analysis of RNASeq from granuloma developed from PBMC of sarcoidosis subjects treated with microparticles vs. PBMC of the same patients treated saline. The results show that the developed granuloma overexpressed several immune genes in Th-1 pathway. IFN-gamma and IFN-gamma R, IL-12R, STAT 1 and STAT 4, and T Bet are overexpressed, but IL-4 and IL-4 R, STAT 5 and STAT 6, were downregulated. (Corrected P value (FDR)<0.01, and Fold Change 2.5).
Figure 5:
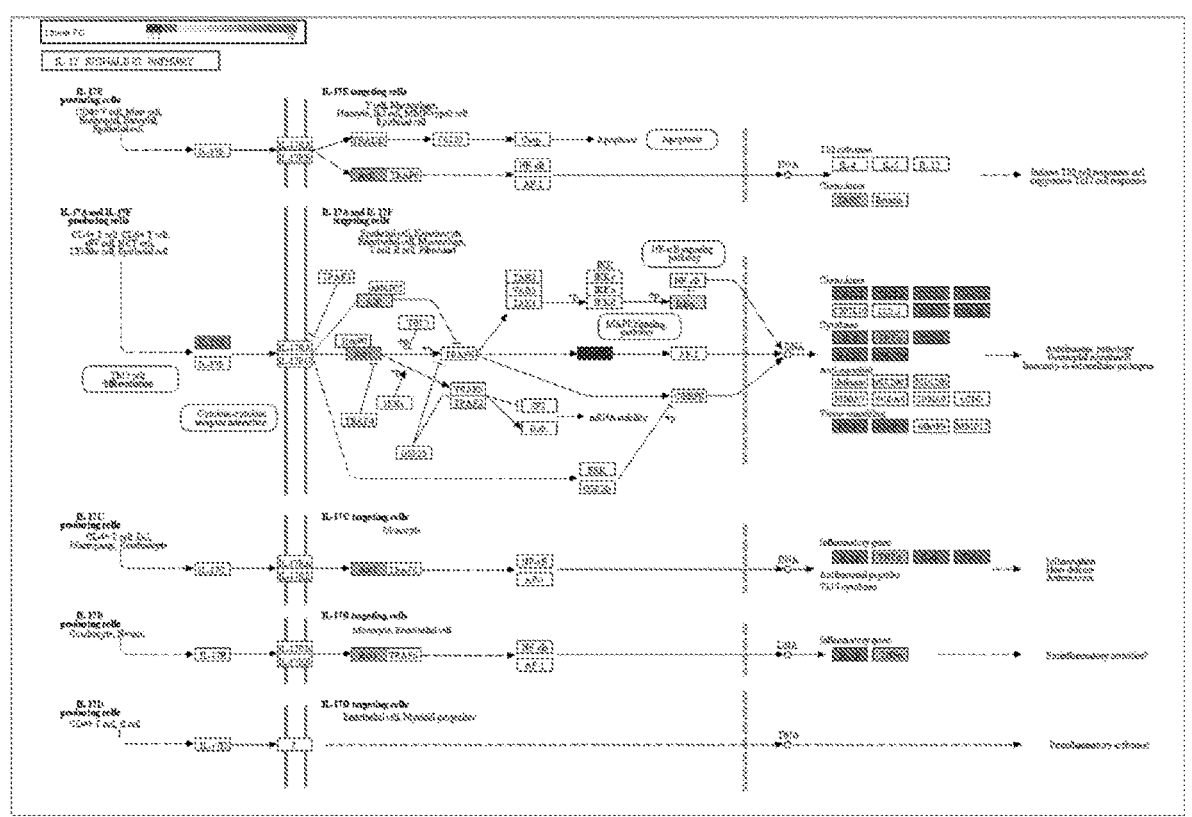
FIG. 5 shows the pathway analysis of RNASeq from granuloma developed from PBMC of sarcoidosis subjects treated with microparticles vs. PBMC of the same patients treated saline. The results show that the developed granuloma overexpressed several immune genes in IL-17 pathway. IL-17A, Act1, and A20 overexpressed, but MAPK downregulated. (Corrected P value (FDR)<0.01, and Fold Change 2.5).

Characterization of the in vitro granuloma model T-helper immunophenotype. Gene expression profile. Given that granuloma from subjects with clinical sarcoidosis have Th1 and Th17 gene expression profiles (Facco M, et al., *Thorax* 2011; 66: 144-150), it was tested whether this occurred as well in the in vitro granuloma model. For this, the induced granulomas were analyzed for gene expression using RNAseq. It was found that the in vitro granulomas had 853 genes that were significantly differentially expressed (FDR <0.05 and FC>2.5) compared to unchallenged PBMC. These genes include IL-1β, IL-2R, IL-6, IL-7, IL-8, IL-10, IL-12, IL-15, IFN-α, IFN-γ, TNF-α, GM-CSF, CCL2, CCL3, CCL4, CCL5, CXCL9 and CCL11 (FIG. 3). Pathway analysis performed on the differentially expressed genes was performed using the iPAthwayGuide software (ADVAITA, Plymouth, Mich.) and confirmed a gene expression profile enriched for the Th1 and Th17 pathways (FIGS. 4 and 5).

Figure 6A:
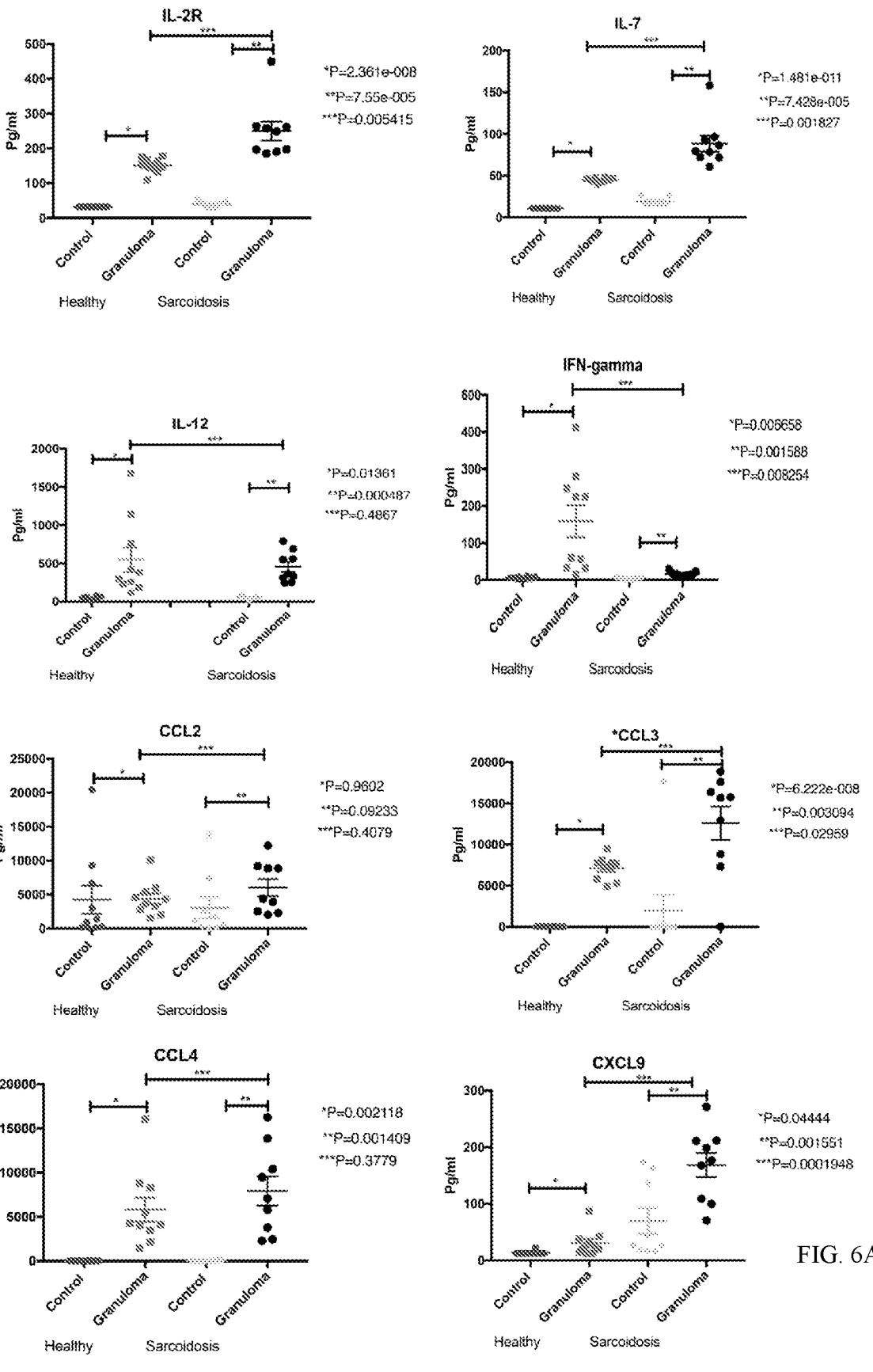
FIGS. 6A-B show secretion of cytokines and macrophage related cytokines in a granuloma developed from PBMC of sarcoidosis subjects and healthy controls.
Figure 6B:
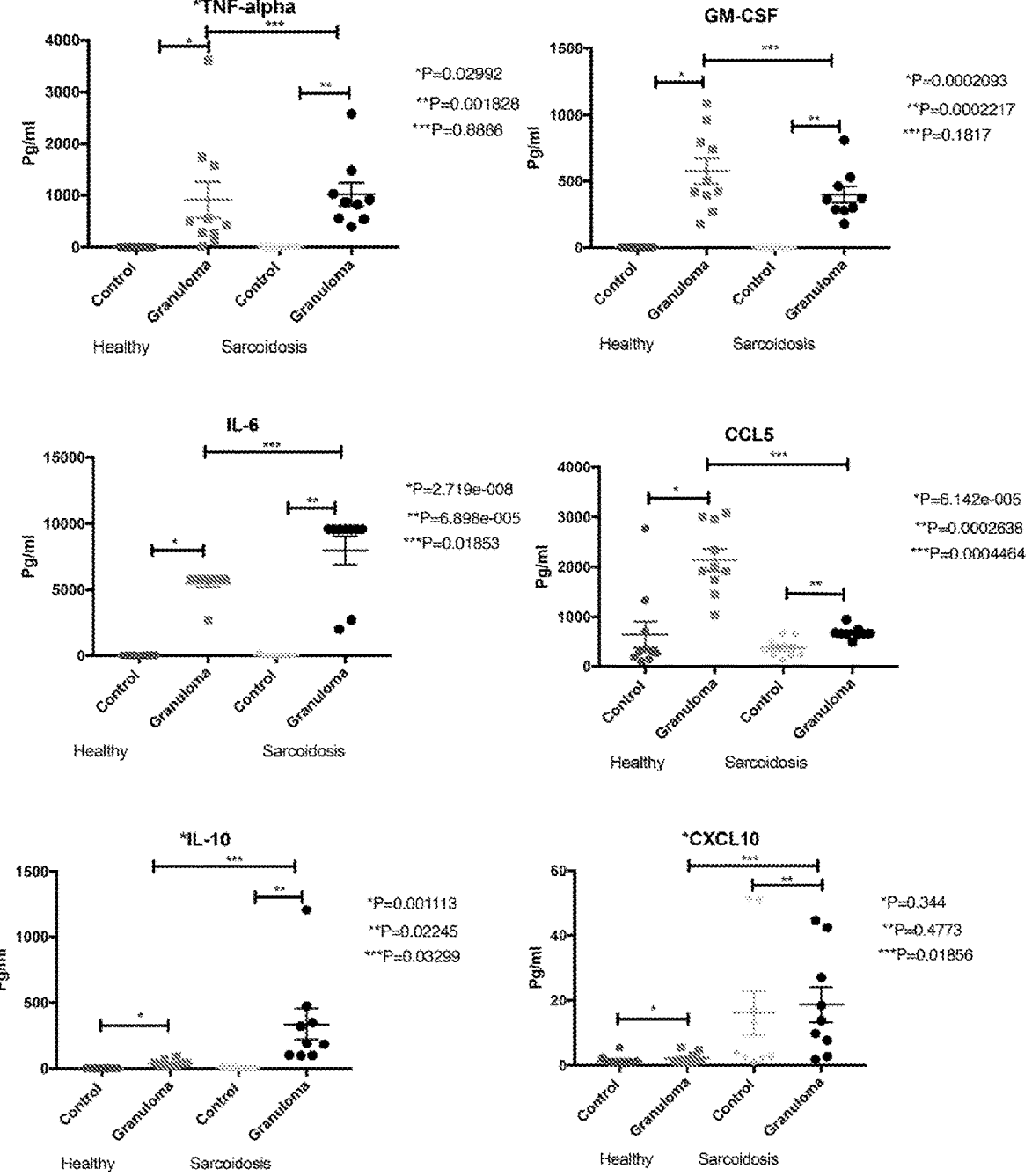

Cytokine profile. The cytokine release profile of the in vitro granuloma model was also evaluated as granulomas in clinical sarcoidosis release cytokines with a Th1 profile (Tsiligianni I, et al., *BMC pulmonary medicine* 2005; 5: 8; and Prasse A, et al., *Clinical and experimental immunology* 2000; 122: 241-248). Supernatants of formed granulomas were collected on Day 3 and analyzed for IL-2R, IL-6, IL-7, IL-10, IL-12, IFN-γ, INF-α, GM-CSF, CCL2, CCL3, CCL4, CCL5, CXCL9, CXCL10 and CCL11 cytokine concentrations using Illumina multiplex ELISA according manufacturer recommendations. FIG. 6 shows that in vitro granulomas released a significantly higher concentration of cytokines compared to equivalent number of unchallenged PMBC. The granuloma model demonstrated a TH1 cytokine profile with increased secretion of IL-2R, IL-7, IL-12, IFN-γ, and TNF-α.

Figure 7A:
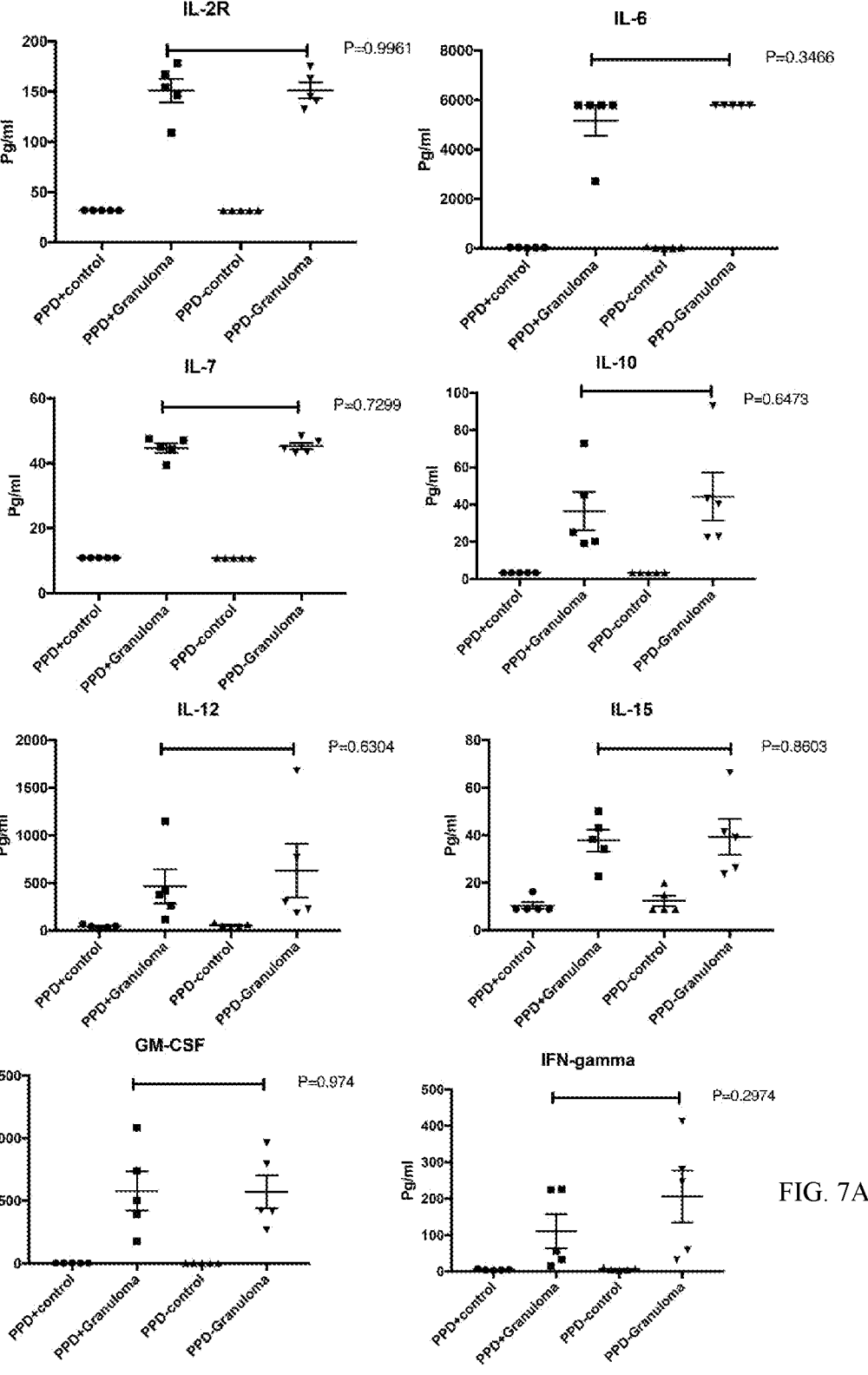
FIGS. 7A-B shows cytokine profiles of PBMC from healthy subjects with and without a positive purified protein derivate (PPD).
Figure 7B:
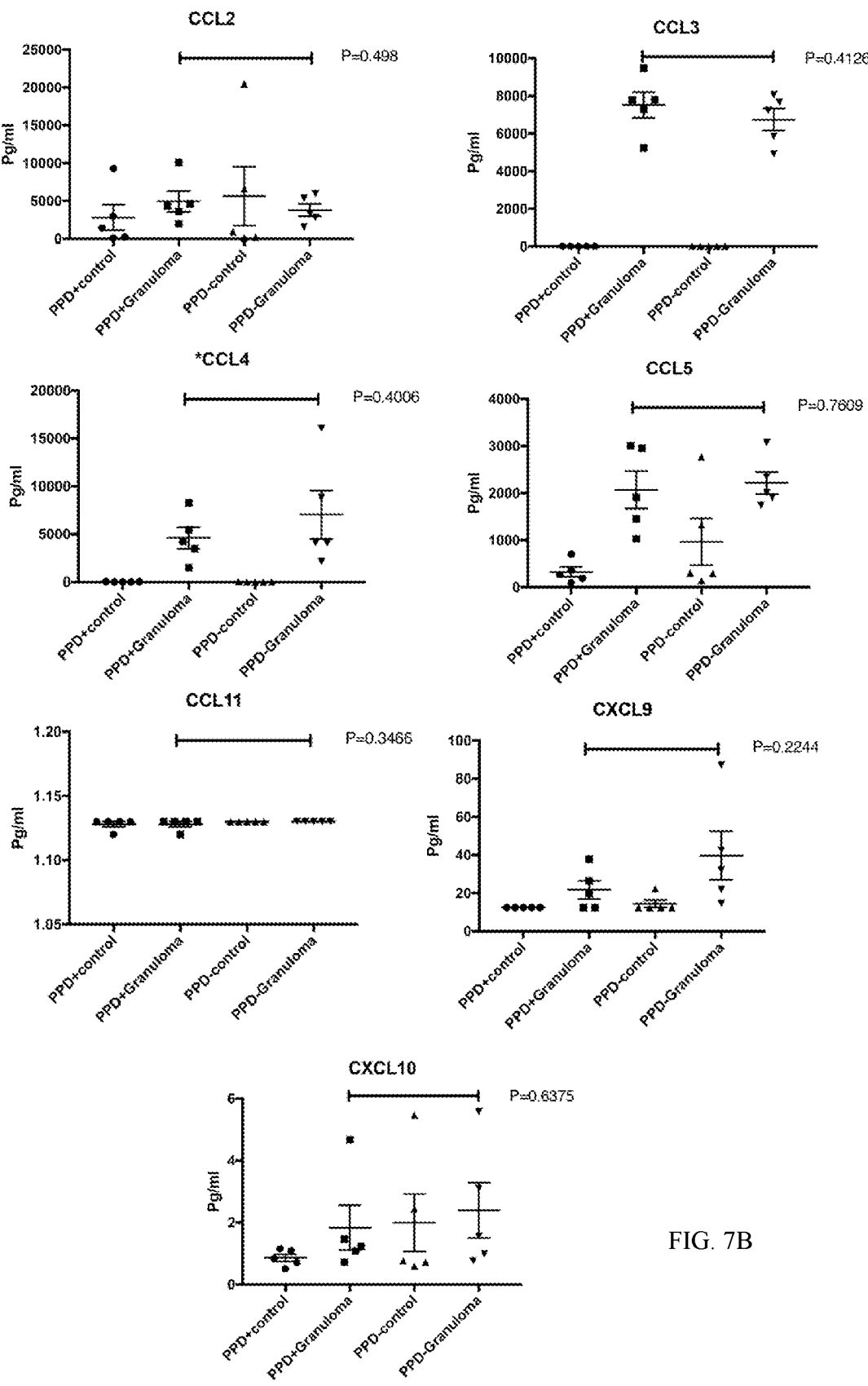

FIG. 6 also shows that the cytokine release profile was more pronounced in granulomas derived from PBMC from sarcoidosis subjects as opposed to healthy controls. These healthy controls were age, gender and race matched to the patients with treatment-naïve sarcoidosis. Overall, the MAB-induced granulomas from sarcoidosis patients expressed higher concentrations of IL-6, IL-7, IL-2R, CCL2, CCL3, CCL4, CXCL9, and CXCL10, but, less IL-12, CCL5 and IFN-γ. Of particular note, granulomas from sarcoidosis patients had a marked decrease in IFN-γ expression compared to healthy controls. The healthy subjects, prior to exposure to mycobacterial antigens, as defined by having a positive purified protein derivate (PPD), did not affected their cytokine release profile (FIG. 7). This data support that sarcoidosis patients have a distinct response to mycobacterial components. This finding may shed light on pathogenesis of sarcoidosis.

Figure 8:
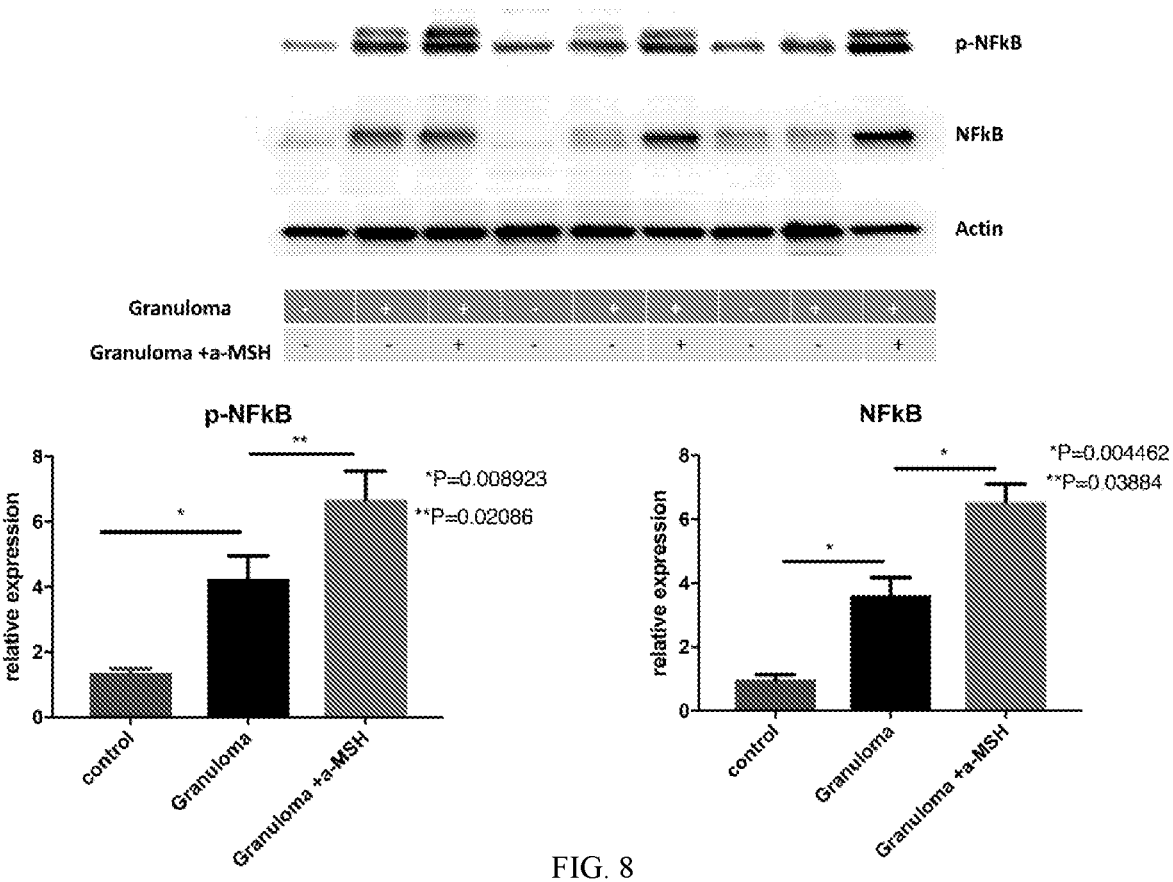
FIG. 8 shows that NFkB and phosphorylated NFkB concentrations increased in granuloma and significantly reduced after treatment with αα-MSH. The granuloma was developed using PBMC of sarcoidosis subjects.
Figure 9:
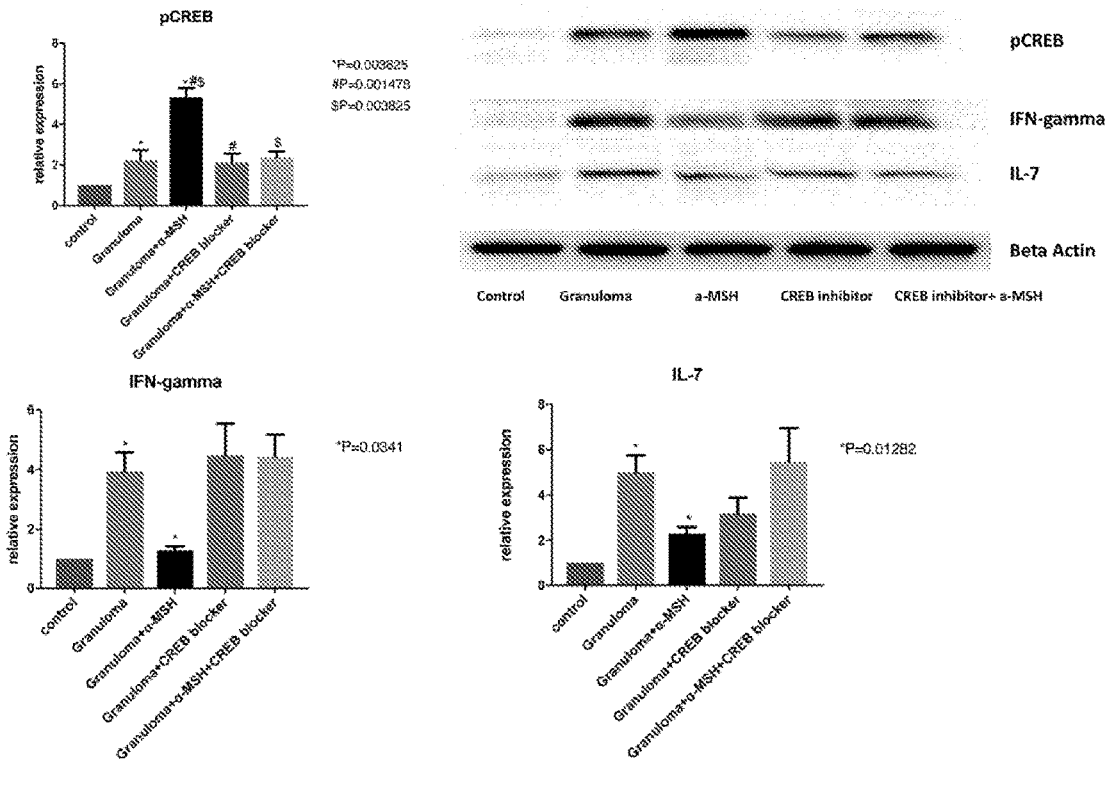
FIG. 9 shows that phosphorylated CREB concentrations increase in the granuloma. This effect was reversible with adding a CREB blocker. Also shown is that the expression of IFN-gamma and IL-7 increased in the granuloma and significantly reduced after treatment with α-MSH. The granuloma was developed using PBMC of sarcoidosis subjects for this experiment.
Figure 10:
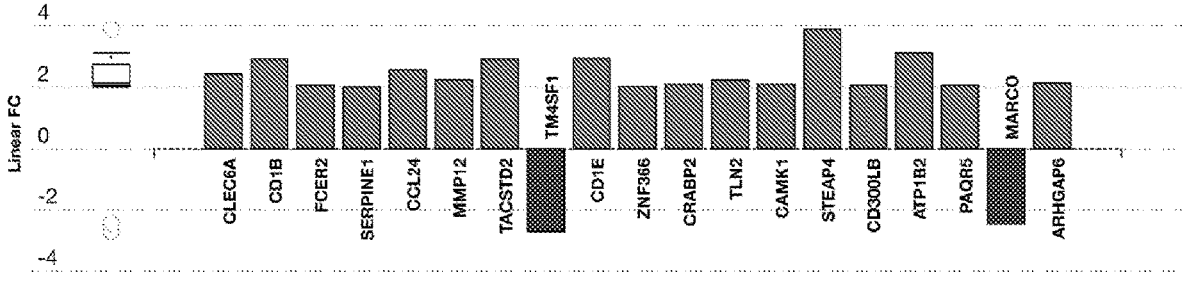
FIG. 10 shows pathway analysis of RNASeq in comparison between the granuloma developed from PBMC of sarcoidosis subjects treated with α-MSH vs. the granuloma developed from PBMC of sarcoidosis subjects with microparticles but treated with saline MARCO was downexpressed with α-MSH in granuloma. (Corrected P value (FDR)<0.01, and Fold Change 2). CLEC6A: C-Type Lectin Domain Containing 6A, CD1B: cluster of differentiation 1, FCER2: Fc epsilon RII, SERPINE1: Serpin Family E Member 1, CCL24: Chemokine (C-C motif) ligand 24, MMP12: Matrix Metalloproteinase 12 (Macrophage Elastase), TAC-STD2: Tumor Associated Calcium Signal Transducer 2, TM4SF 1: Transmembrane 4 L6 family member 1, CD1E: cluster of differentiation 1 E (T-cell surface glycoprotein), ZNF366: Zinc finger protein 366, also known as DC-SCRIPT (Dendritic cell-specific transcript), CRABP2: Cellular retinoic acid-binding protein 2, TLN2: Talin 2, CAMK1: Calcium/calmodulin-dependent protein kinase type 1, STEAP4: STEAP4 Metalloreductase, CD300LB: CD300 Molecule Like Family Member B, ATP1B2: ATPase, Na+/K+ transporting, beta 2, PAQR5: Progestin And AdipoQ Receptor Family Member 5, MARCO: Macrophage Receptor With Collagenous Structure, ARHGAP6: Rho GTPase Activating Protein 6.
Figure 13:
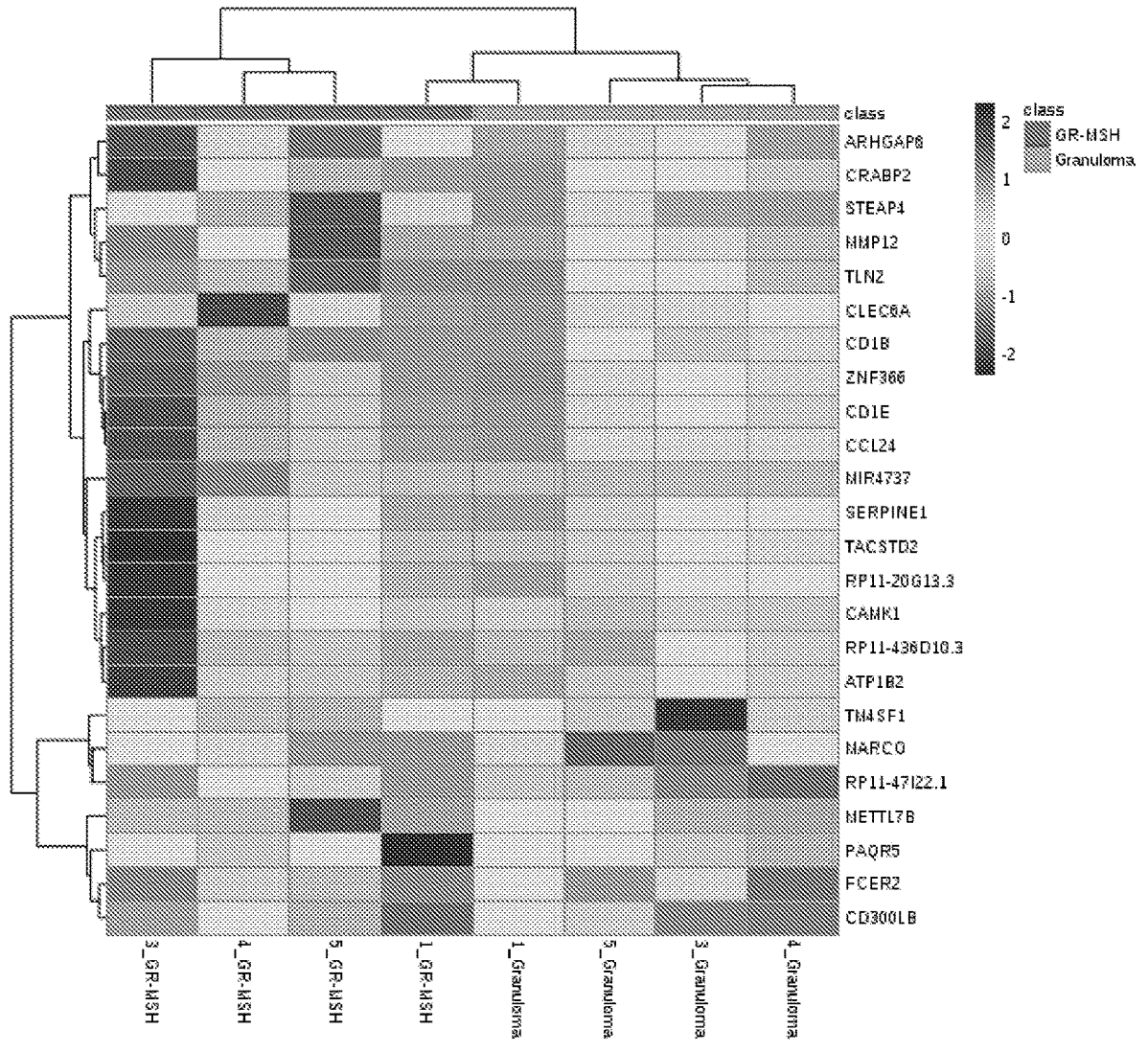
FIG. 13 shows the heatmap for genes in comparison between a granuloma developed from PBMC of sarcoidosis subjects treated with alpha-MSH vs. a granuloma developed from PBMC of sarcoidosis subjects with microparticles but treated with saline (Corrected P value (FDR)<0.01, and Fold Change 2). Granuloma: developed from PBMC of sarcoidosis subjects with microparticles treated with saline, GR-MSH: granuloma developed from PBMC of sarcoidosis subjects treated with alpha-MSH.

NFkB expression. The heightened T-cell immunophenotyped of the in vitro granulomas was associated with a significantly higher protein expression for total NFkB, and phosphorylated NFkB (p-NFkB) compared to unchallenged PBMC from subjects with sarcoidosis. It was also observed that the phosphorylated version of the cAMP response element-binding protein (p-CREB), a transcription factor capable of binding DNA and regulating gene expression, was significantly down-expressed in the in vitro granulomas as shown in FIGS. 8 and 9. This suggests that p-NFkB plays a central role in the induction of inflammation after exposure to microparticles. Given toll like receptor (TLR)-4 and macrophage receptor with collagenous structure (MARCO) gene expressions significantly downregulated in granuloma in RNA-Seq, it was concluded that NFKB activations stimulated via these receptors.

α-MSH exerts anti-inflammatory effects on MAB-induced in vitro granulomas. To evaluate the potential anti-inflammatory effects of α-MSH in sarcoidosis inflammation, its effects were tested on the in vitro granuloma model using PBMCs from subjects with sarcoidosis exposed to MAB particles. RNA-Seq analysis was performed at day 3 after exposure or not to 10 μM α-MSH. FIG. 10 shows genes that were differentially expressed in granuloma with α-MSH treatment. FIG. 11 shows pathway analysis of 21 genes that up- or down-regulated after α-MSH in granuloma. RT-PCR analysis was also performed at day 3 after exposure or not to 10 μM α-MSH. It was observed that RNA expression of IL-7, IL17A, IL6, MARCO, IFN-γ, and IL-8 was significantly decreased in granulomas treated with α-MSH (FIG. 12). Furthermore, RNA-seq analysis showed significant changes in gene profiles between two groups as shown in heatmap (see FIG. 13).

Figure 14:
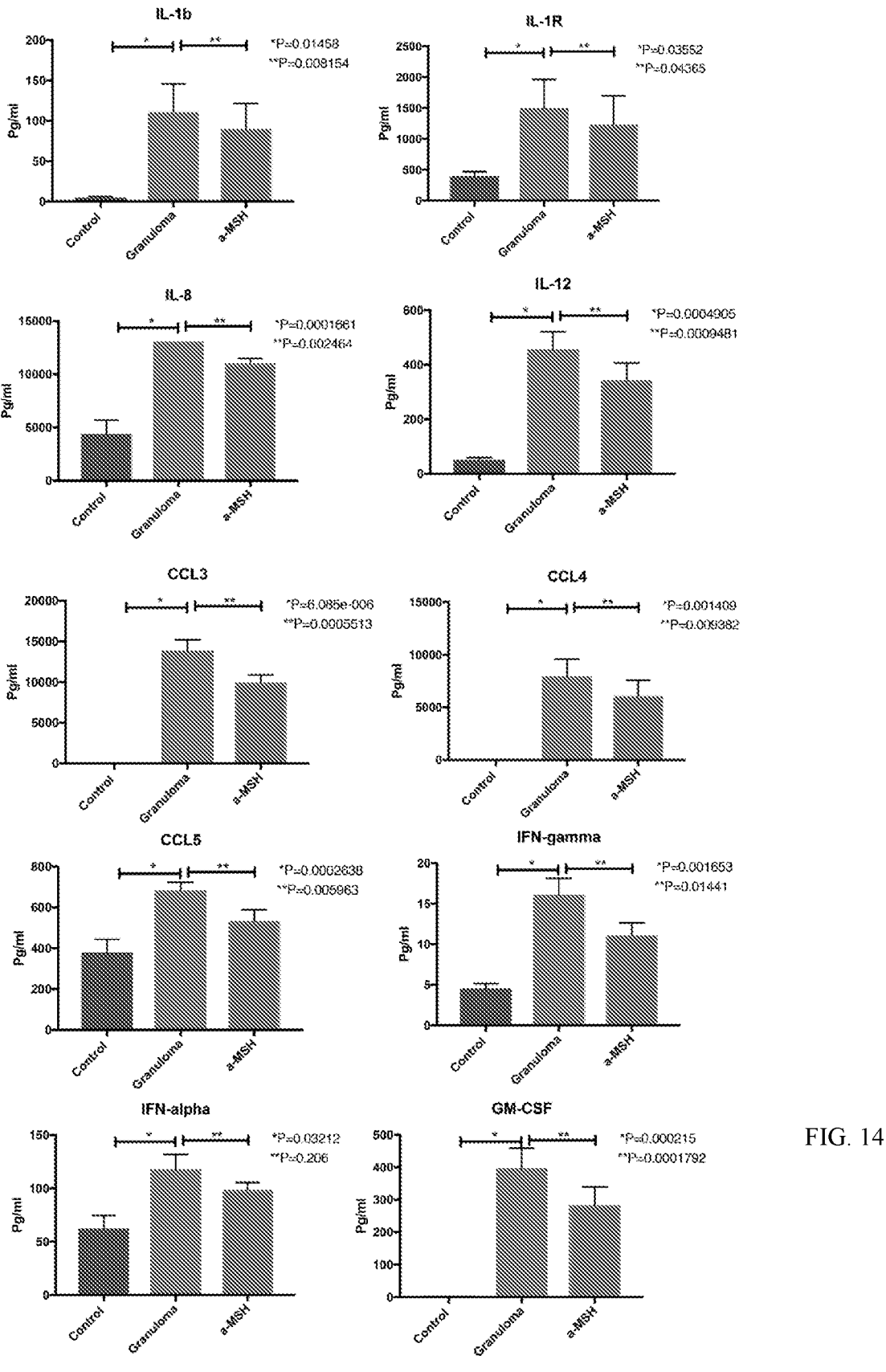
FIG. 14 shows cytokine production of a granuloma developed from PBMC of patients with sarcoidosis. Control DO: PBMC without challenging with microparticles in the day of starting experiment. Control D3: PBMC without challenging with microparticles in the day of 3. Granuloma was challenged with 10 μM of α-MSH.
Figure 15:
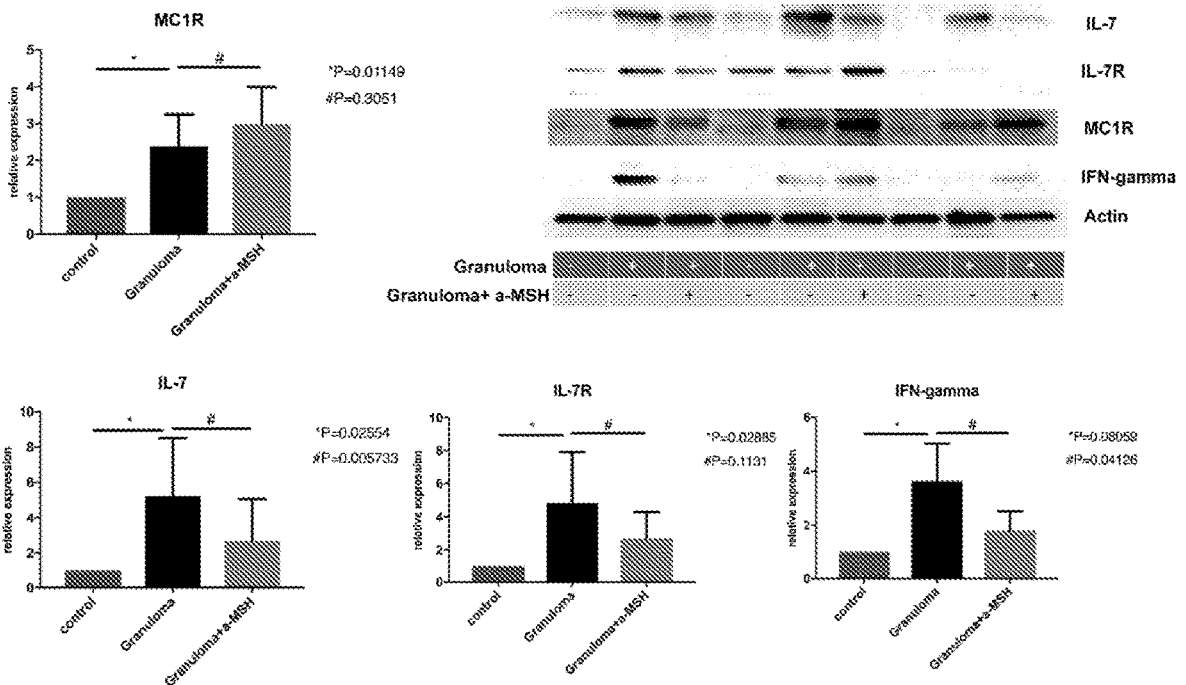
FIG. 15 shows protein expression using western blot in control, granuloma and granuloma treated with α-MSH.

Confirmatory protein expression analysis confirmed IL-1b, IL-1R, IL-8, IL-12, CCL3, CCL4, CCL5, GM-CSF, IFN-γ, and TNF-α were significantly reduced in granuloma treated with α-MSH (see FIG. 14). FIG. 15 shows results for other cytokines tested.

Figure 16:
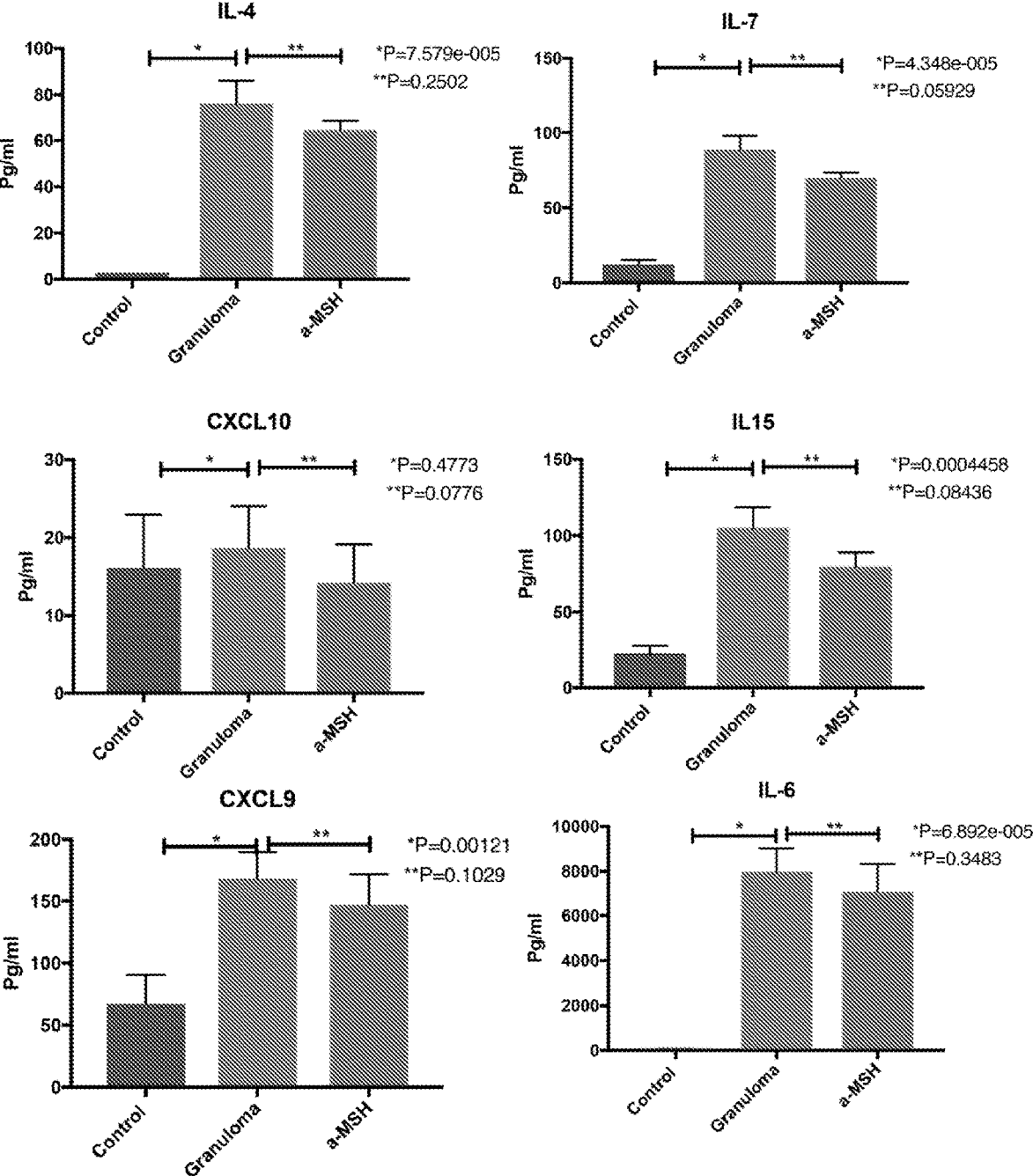
FIG. 16 shows cytokine production of granuloma developed from PBMC of patients with sarcoidosis. Control DO: PBMC without challenging with microparticles on the day of starting the experiment. Control D3: PBMC without challenging with microparticles on day 3. Granuloma was challenged with 10 μM of α-MSH.

Since α-MSH belongs to melanocortin 1 receptor (MC1R) agonist family, an anti-MC1R antibody was used to assess western blots in PBMC, granulomas, and granulomas treated with α-MSH cells. It was found that MC1R expression was significantly increased in granulomas but no significant changes occurred after exposure to α-MSH as shown in FIG. 16.

α-MSH reduced inflammation in the in vitro granulomas by inducing phosphorylation of CREB. Given that p-CREB acts as an important inhibitor of the P300–CREB binding protein coactivator family involved in the transcription of inflammatory mediators (Wen A Y, et al., *Journal of immunology* 2010; 185: 6413-6419), and the observation of p-CREB reduction in granulomas, it was tested whether induction of p-CREB could be a mechanism of action of α-MSH. For this, intracellular p-CREB concentrations were measured in granulomas treated and untreated with α-MSH, and a control group. The data support that developed granulomas treated with α-MSH increased the concentration of p-CREB significantly (FIG. 9). Addition of 666-15, a potent and selective CREB inhibitor (IC50=81 nM, Sigma-Aldrich, Millipore), significantly blocks the anti-inflammatory effect of α-MSH (FIG. 9). This strongly suggests that CREB phosphorylation is important for α-MSH signaling.

Discussion Described herein is an in vitro model to study sarcoidosis. By challenging PBMC with microparticles generated from MAB cell wall, well-formed granulomas, with clear TH1 and Th17 inflammatory profiles based on gene expression and cytokine secretion studies, were induced. It was also found that α-MSH exerts anti-inflammatory effects on this granuloma model with a clear reduction in IL-7, IL-7R, and IFN-γ. This therapeutic effect was CREB dependent and reversible using a specific CREB activation inhibitor.

Sarcoidosis causes inflammation in the lung and triggers a complex cascade of immunopathologic events, including leukocyte recruitment and granulomata formation. Subsequent abnormal repair processes lead to structural changes such as pulmonary remodeling of the lung parenchyma, airway, and vascular systems (Nagai S, et al., *Clinics in chest medicine* 2008; 29: 565-574; and Iannuzzi M C, et al., *JAMA*, 2011; 305: 391-399) which result in permanent structural and physiological changes. In about a third of patients (Lockstone H E, et al., *American journal of respiratory and critical care medicine* 2010; 181: 1367-1375), subjects develop fibrotic pulmonary sarcoidosis that is life-threatening. In sarcoidosis, macrophages and lymphocytes play a role in the inflammatory cascade, both activated by unknown agents on airway epithelium cells and immune cells (Zhang S, et al., *Laboratory investigation; a journal of technical methods and pathology* 1999; 79: 395-405). The mechanism involved in granuloma formation is not well known. However, it has been suggested that cytokines including (IL-2, IL-7, IL-8, IL-12, IFN-γ, TNF-α, and GM-CSF) have a role in initiation and continuation of granuloma. Crouser and co-workers developed an in vitro granuloma model using purified protein derivate (PPD) of *mycobacterium tuberculosis* (Crouser E D, et al., *American journal of respiratory cell and molecular biology* 2017; 57: 487-498). They showed that PBMC react to coated beads with PPD and then aggregated and formed granuloma. The data provided here suggest that the granuloma model described herein is more relevant to study sarcoidosis as it used a more prevalent antigen (NTM is more prevalent than TB and are environmental) and the granulomas are immunophenotypical similar to granulomas in clinical sarcoidosis.

Melanocortin signaling peptides (melanocortins) consist of the adrenocorticotropin hormone (ACTH), α-MSH, beta-melanocyte-stimulating hormone (I3-MSH), and gamma-melanocyte-stimulating hormone (γ-MSH). Melanocortins are derived from the proopiomelanocortin (POMC) prohormone, which is post-translationally modified by proconvertase 1 or 2 to generate each peptide (Benjannet S, et al., *Proceedings of the National Academy of Sciences of the United States of America* 1991; 88: 3564-3568). Processing of POMC is specific to the tissues and cells in which it is expressed. Melanocortins contain the amino acid sequence His-Phe-Arg-Trp (SEQ ID NO: 1), which is integral to their biological function (Gantz I, et al., *Am J Physiol Endocrinol Metab* 2003; 284: E468-474). α-MSH is a 13 amino acid peptide most known for its cutaneous neuroimmunomodulatory response to ultraviolet light that leads to increased skin pigmentation and has further been shown to possess anti-inflammatory (Lipton J M, et al., *Immunol Today* 1997; 18: 140-145) and anti-microbial effects (Cutuli M, et al., *Journal of leukocyte biology* 2000; 67: 233-239). This is the first report of the anti-inflammatory effect of α-MSH on granulomatous inflammation.

The melanocortin 1 receptor (MC1R) was originally referred to as α-melanocyte stimulating hormone receptor (the name of its major ligand) though it has equal affinity for ACTH (Chhajlani V, et al., *Biochemical and biophysical research communications* 1993; 195: 866-873). MC1R is expressed in the immune system, gut, testis, ovary, placenta, lung, liver, and skeletal muscle. Specifically, MC1R is found on endothelial cells, monocytes, macrophages, lymphocytes, neutrophils, mast cells, intestinal epithelia, among many others (Brzoska T, et al., *Endocr Rev* 2008; 29: 581-602). MC1R has also been shown to play a role in inflammation. Certain polymorphisms in the MC1R affect the degree of sepsis in patients who have experienced trauma (Seaton M E, et al., *Shock* 2017; 47: 79-85). It has been shown that signaling through MC1R attenuates IL-8 and TNF-α-mediated inflammatory responses (Taherzadeh S, et al., *The American journal of physiology* 1999; 276: R1289-1294). The role of this receptor in pathogenesis of sarcoidosis has not been previously studied.

One of the effects of α-MSH is decreasing the expression of the MARCO. MARCO is a class A scavenger receptor (SR) that senses and clears pathogens through the recognition of pathogen-associated molecular patterns (PAMPs). MARCO is known for recognizing polyanionic particles in nature, including environmental particles, nucleic acids, bacterial lipopolysaccharides, oxidized lipoproteins, and numerous endogenous proteins (Arredouani M S. et al., *Oncoimmunology* 2014; 3: e955709). Many of these ligands are also recognized by and trigger cell signals through Toll-like receptors (TLR) (Kissick H T, et al., *PloS one* 2014; 9: e104148). Recently it was demonstrated that TLR-signaling is finely tuned by MARCO expressed on macrophages (Bowdish D M, et al., *PLoS pathogens* 2009; 5: e1000474). MARCO internalize antigens to render them accessible to TLR3, TLR7/8 and TLR9 localized in the cytosol but limit response via TLR4 (Mukhopadhyay S, et al., *Blood* 2011; 117: 1319-1328). Although the role of MARCO in sarcoidosis has not been studied, TLRs have a known role in the pathogenesis of sarcoidosis. It was shown that a variant within or close to the TLR4 gene may increase susceptibility to sarcoidosis (Schurmann M, et al. *Clinical and experimental immunology* 2008; 152: 423-431). In animal models, TLR2 gene deletion was found to be an important receptor in the development of granuloma formation. TLR2 (−/−) mice showed significantly attenuated granuloma inflammation to heat-killed *Propionibacterium acnes* (Gabrilovich M I, et al., *Clinical and experimental immunology* 2013; 173: 512-522).

TLR4 is an important receptor for innate immunity against chronic Mycobacterial infections (Abel B, et al., *J Immunol* 2002; 169: 3155-3162). Signaling via TLRs activates NFKB with phosphorylation and degradation of inhibitory (IkappaB) (Kawai T, Akira S. et al., *Trends Mol Med* 2007; 13: 460-469; and Vu A, et al., *Eur J Pharmacol* 2017; 808: 1-7). It is concluded that the observed activation of NFKB in granuloma could be due to TLR signaling.

It was observed that treatment with α-MSH is anti-inflammatory, enhancing NF-kB and enhancing p-CREB expression. CREB is a known transcription factor that mediates the transcription of genes containing a cAMP-responsive element. Signaling through G-protein-coupled receptors (GPCRs) induces activation of CREB (Li J, et al., *Nature* 2002; 420: 716-717; and Rosenbaum D M, et al., *Nature* 2009; 459: 356-363). Given that MC1R is known as GPCR (Yang Y. et al., *Eur J Pharmacol* 2011; 660: 125-130), overexpression of CREB and p-CREB after α-MSH treatment is expected.

CREB signaling is involved in the regulation of cellular proliferation, survival, and differentiation and the transcription of several immune-related genes such as IL-2, IL-6, IL-10, and TNF-alpha as well as macrophage and lymphocytes survival (Wen A Y, et al., *Journal of immunology* 2010; 185: 6413-6419; and Shaywitz A J, Greenberg M E. CREB: et al., *Annual review of biochemistry* 1999; 68: 821-861). Phosphorylated CREB occurs in response to cellular stress or growth factors and limits proinflammatory responses by directly inhibiting NF-kB activation by blocking the binding of CREB binding protein to the NF-kB complex.

Others have shown that α-MSH suppresses NFkB activation (Luger T A, et al., *Annals of the rheumatic diseases* 2007; 66 Suppl 3: iii52-55). As described here, it was found that, in the disclosed sarcoidosis model, α-MSH is anti-inflammatory by inducing p-CREB despite NF-kB remaining active. It is thought that longer duration of treatment with α-MSH in the model disclosed herein (3 days) vs. short exposure (15 min) in their study made paradoxical results on NF-kB concentration levels.

Conclusion. The results described herein showed in the in vitro granuloma model, α-MSH has anti-inflammatory properties in which a significant reduction of IL-7, IL7R, and IFN-γ and CCL3, via downregulation of MARCO (gene and protein), and induction of phosphorylation of CREB. This is a potential therapeutic agent for the treatment of persistent inflammation in sarcoidosis.

Materials and Methods.

MAB microparticle development. MAB cell wall microparticles were isolated from a strain of MAB with a rough colony isolated from sputum of 11-year old boy with cystic fibrosis (isolate # CCUG 47942). MAB was grown in middlebrook 7 h9 broth with ADC enrichment medium (Millipore Sigma, St. Louis, Mo., USA) at 37° C. Cells were collected when OD600 reach to 1.0-1.2 by centrifugation at 4000 g for 10 minutes, washed once in PBS, centrifuged and resuspended using a 15 to 1 (volume to volume) ratio of lysis buffer, sonicated and incubated on ice for thirty minutes. The lysis buffer contains 137 mM sodium chloride, 10 mM Na phosphate, 2.7 mM potassium chloride; combined with detergents and protease inhibitors. Lysed cell samples were then centrifuged at 3000 g for 5 minutes to remove intact MAB cells. The supernatant was transferred to a new tube and centrifuged for 20 minutes. 20 ml fresh lysis buffer was and the pellet was resuspended by brief sonication and centrifuged at 12,000 g for another 20 minutes. The pellet was resuspended in 20 ml volume of PBS and kept at 95° C. for 15 min. After cooling to room temperature, the lysate was centrifuged at 12,000 g for 20 minutes and the pellet was washed with PBS buffer 3 times at 12,000 g for 10 minutes. Finally, the pellet was suspended in Dulbecco's Modified Eagle Medium (DMEM) and stored at −80° C. The concentration of the microparticles was calculated by the following equation: Final concentration=Volume of original culture×OD600× (2.2×108 bacteria/ml)/final volume. High quality images of non-infectious, MAB particles were obtained by scanning electron microscope (SEM).

Human blood sample. Blood samples were collected from 9 patients with confirmed pulmonary sarcoidosis and were randomly selected from the University of Miami Sarcoidosis Biobanking, and matched by age, sex and race with 10 healthy controls. To avoid the inconvenience and risks associated with additional venipunctures, a 10 ml blood specimen was collected during an already scheduled venipuncture. Patients who currently have a hgb <7 mg/dL were be excluded from participating.

PBMC isolation. PBMCs are isolated from whole blood using a fully-closed system with Ficoll™ Hypaque™ Solution offered by BD Biosciences, USA (Vacutainer® CPT™ Mononuclear Cell Preparation Tube—Sodium Citrate) per manufacturer recommendation and previous protocols (Baechler E C, et al., *Proceedings of the National Academy of Sciences of the United States of America* 2003; 100: 2610-2615; and Green L J, et al., *Clinical cancer research: an official journal of the American Association for Cancer Research* 2006; 12: 3408-3415).

Cell culture. Methods of cell culture for PBMC were used. Isolated PBMCs are cultured in RPMI 1640 medium containing 10% autologous serum in 100-by-15-mm or 24-well tissue culture dishes at 37° C. in a 5% $CO_2$ atmosphere. A total of $2\times10^6$ PBMCs/ml (containing approximately $2\times10^5$ monocytes), were immediately infected with MAB cell wall microparticles at a MOT of 10:1 in the presence of 10% autologous serum and incubated for up to 7 days, during which time granulomas were developed and studied. Media and serum was replenished every 2 days. Use of autologous serum allows for retention of the undefined characteristics that are uncommon to each individual.

Bacterial culture and microparticle development. Briefly, the visible MAB on liquid media were collected, washed with PBS and sonicated in lysis buffer (PBS with 0.1% sds, 10 mM EDTA). To remove the intact cells, we pelleted them by centrifuging for 5 minutes at 3000 rpm in tabletop centrifuge. Supernatant was carefully removed and centrifuged again for 20 min at 10,000 rpm to pellet cell wall particles. Pellet was washed one more time with lysis buffer and centrifuged again. Pellet was washed with PBS contain 1% SDS, 10 mM EDTA at heated for 15 min at 95° C. SDS and EDTA was used to remove contaminating protein and materials ionically-bound to the cell wall. The pellet was washed with PBS and centrifuging. The microparticles were finally suspend in PBS. Concentrated suspension of microparticles was cultured in the Lowenstein-Jensen medium confirming that intact live bacteria did not pass through the process.

Staging in-vitro granuloma like formation. The stage of granuloma formation is determined semi-quantitatively daily (for 7 days in total) for each experimental group (Guirado E, et al., mBio 2015; 6: e02537-02514). In summary, each sample are assessed by light microscopy (Olympus IX71 DP71 microscope digital camera). At least 15 separate high-power fields per sample are evaluated, and at least 3 replicates are used to establish a scoring index. The score was calculated as the mean of the sum of granuloma scores for each sample. Stage 1: No cellular aggregation, Stage 2: cellular aggregation starts diameter of the base less than 25 micrometer, stage 3: diameter of the base: 25-100 micrometer, Stage 4: the recruited cells from multilayers, comprising macrophages and lymphocytes diameter base 100-200 micrometer, and Stage 5: the cellular structure shows signs of cellular differentiation, multinucleated giant cells presence and diameter of the base is >200 micrometer.

ELISA. Supernatant aliquot samples to be analyzed were collected, thawed and spun at 12,000 rpm for 10 min to separate the particulate material at the bottom. 50 µl of undiluted plasma was plated from each sample onto a 96-well V-bottom plate (source plate) by manual pipetting according to predefined maps. The aliquots were wrapped in parafilm and kept in a humid chamber at 4° C. during the entire process, but not longer than 72 hr. Growth factors and their receptor's capture antibodies were reconstituted and diluted per manufacturer specification and 50 µl were plated into each well of respective 96-well high-binding half-well plates which were then sealed and incubated overnight at 4° C. Alternatively, many plates can be dried at 37° C. and stored at 4° C. for later use, depending on the stability of the protein. ELISA is completed per manufacturer protocol (with volumes adjusted for plates with half-area wells) and the optical density of each well was read using a plate reader set to the appropriate wavelength and analyzed. Cytokines were measured by Human Cytokine Magnetic 25 plex Panel from Life technologies (Carlsbad, Calif.).

Western blot. Total PBMC, granuloma, and granuloma treated with α-MSH cells' extracts are prepared using NP-40 lysis buffer (50 mM Tris, PH 8.0, 1.0% NP-40, 150 mM NaCl, 2 mM EGTA, 2 mM EDTA, protease inhibitor tablet (Roche Molecular Biochemicals, Indianapolis, Ind.), 50 mM Sodium fluoride, and 0.1 mM sodium vanadate), and protein concentrations determined (Bradford method; kit from Pierce). SDS-PAGE separated proteins are electrophoretically transferred to immobilon-P membranes (Millipore Corp. Bedford, Mass.) and incubated in 5% nonfat dry milk, PBS, and 0.25% Tween-20 for 1 h. Membranes are incubated with primary antibodies overnight at 4° C., rinsed, incubated with horseradish peroxidase-conjugated secondary antibody, and then exposed to X-ray film (X-Omat, Eastman Kodak Co.) for analysis, using enhanced chemiluminescence (ECL Plus, Amersham Pharmacia Biotech, Arlington, Heights, Ill.). Actin protein was measured as a loading control. Antibodies used for anti-NFkB. And anti-p-NFkB were purchased from cell Signal (Danvers, Mass.), anti-CREB from Abcam (Cambridge, UK) CREB INHIBITOR, 666-15 from Sigma (St. Louis, Mo.), anti-IL-7 from Proteintech (Rosemont, Ill.), CD68, CD4 from Abcam (Cambridge, UK), Anti-MC1 Receptor from Jerusalem, Israel), anti-IL7R Santa Cruz Biotechnology (Dallas, Tex.), anti-IFN-gamma from Proteintech (Rosemont, Ill.).

RNA isolation and analysis. RNA isolation was carried out using a kit from ZymoResearch, Irvine, Calif. USA following the manufacturer recommendations.

RNA Sequencing at the John Hussman Institute for Human Genomics (HIHG) Center for Genome Technology (CGT). RNA-seq for whole transcriptome analysis: Preparation of transcriptome libraries for sequencing on the Illumina NextSeq500 platform was carried out at CGT using established RNA-seq methods. Briefly, 200 ng of total RNA via Agilent Bioanalyzer was prepped for sequencing using a NuGen Universal RNA library preparation kit including AnyDeplete probes to remove ribosomal RNA according to manufacturer's protocol. Samples were barcoded to allow for multiplexing. Cluster generation and sequencing took place on the Illumina NextSeq500 using the reagents provided by Illumina, targeting 25 million single-end 75 base reads per sample.

FASTQ files were generated by HiSeq's Real Time Analysis (RTA) followed by a BCL2FASTQ script supplied by Illumina and then processed through a bioinformatics pipeline. This consists of initial quality control of the reads via FastQC to determine basic quality metrics including per base quality, GC content, and sequence read lengths and distribution. Trimming of the sequences for bad quality bases, adapter and primer sequences were performed using TrimGalore! software. Alignment to the GRCh38 human reference genome will be done using STAR v2.5.2a aligner; other methodologies such as HiSat2 or TopHat2 are also be considered. The GeneCounts module within STAR was used for gene quantification against the current GENCODE gene definition (currently v28); StringTie and Cufflinks gene quantification was considered as appropriate. Differential expression was performed using the DESeq2 software package and pathway analysis based on expression results performed using a variety of programs including DAVID and Ingenuity Pathway Analysis.

The CGT is also equipped with molecular biology (PCR) capabilities, which was used for expression verification and validation. RNASeq analysis isolated from PBMC, granuloma cells, granuloma treated with α-MSH were analyzed in CGT.

In vitro sarcoid-like granuloma was developed with challenging PBMC of patients with confirmed sarcoidosis and treatment-naïve with microparticles generated from *Mycobacterium abscessus* cell wall. PBMC, and developed granuloma were treated daily with 1 μM and 10 μM of α-MSH (MILLIPORE-SIGMA, St. Louis, Mo., USA) or saline as control. The supernatants of developed in vitro granuloma treated with saline and α-MSH were collected on Day 3. The cytokine concentrations were measured using Illumina multiplex Elisa as mentioned previously. The PBMC, granuloma and granuloma+α-MSH cells from were harvested and cellular protein was extracted for western blotting. To determine the anti-inflammatory effects of α-MSH on granuloma protein and gene expressions of IL-7, IL-7R, IFN-γ, MC1R, NFkB, and phosphorylated NFKB (p-NFkB), MARCO, and p-CREB were measured with western blot and RNAseq respectively, and stored frozen inside a −80 freezer no longer a year after isolation.

RT-PCR. RT-PCR was performed. MARCO, IL-6, IL-7. IL-8, IL17A, IFN-gamma were analyzed.

Example 2: Development of a Sarcoidosis Mouse Model

Culturing peripheral blood mononuclear cells (PBMCs) with mycobacterial cell wall microparticles led to the development of an in vitro sarcoid-like granuloma model. PBMC samples isolated from 9 patients with confirmed pulmonary sarcoidosis were challenged with *Mycobacterium abscessus* (MAB) cell wall microparticles purified (30) with modifications. As shown in FIG. 1, MAB cell wall particle sizes are less than sub-micron to 2 μm.

The PBMCs used in this model were obtained from confirmed treatment-naive sarcoidosis patients with a negative IFN-γ release assay (IGRA) for tuberculosis. PBMCs were isolated from whole blood samples (31), and $5\times10^6$ cells were cultured in RPMI 1640 medium containing 10% autologous serum in 24-well tissue culture dishes at 37° C. in a 5% $CO_2$ atmosphere for 3 days. Microparticles with an equivalent multiplicity of infection (MOI) of 10:1 (and a total endotoxin level of 1.115 EU/ml) were added to the PBMCs in the same day they were cultured. At day 3, mature granulomas were present microscopically. FIG. 2 shows immunohistochemistry stains for macrophage and lymphocytes in the developed granulomas.

Figure 17:
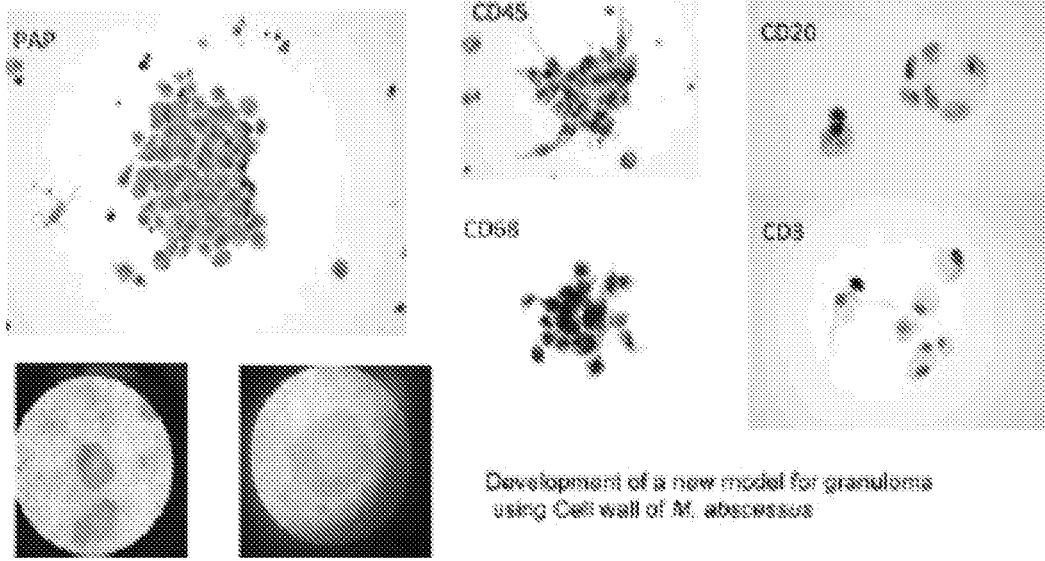
FIG. 17 shows the developed granuloma from PBMCs of sarcoidosis patient stained with Papanicolaou (PAP); stained for CD45 and CD68 to locate macrophages; and stained with CD20 and CD3 to locate lymphocytes. Two microscopic pictures in the left lower show portion of the figure show the actual granuloma in the cell culture plate.

As shown in FIGS. 2 and 17, an in-vitro model for granuloma formation with exposure of human peripheral blood mononuclear cells (PBMCs) to microparticles was generated from *Mycobacterium abscessus* cell wall (microparticles) akin to sarcoidosis. These microparticles will be used to induce TH1 and TH17 granulomatous inflammation in the lungs of mouse. To this end, a mouse model of sarcoidosis using microparticles was developed.

Establishment of lung sarcoidosis model. A mouse model of pulmonary sarcoidosis was established in C57Bl/6 mice. To accomplish this, prepared microparticles were administered intratracheally to a mouse. The mouse's tongue was pulled out with a small spatula and one or more microparticles were inserted into the trachea using a 20 G angiocatheter tube. At the time of laryngeal opening, the spatula was advanced to the main bronchus until resistance was reached. After tube placement, microparticles (microparticle, first dose: 50 microL=$5\times10^8$, followed by up to 3 doses of 20 microL=$2\times10^8$ of CFU of *M. abscessus*). The control group will receive 20 μL PBS intratracheally. FIG. 18 shows the steps for this procedure.

Figure 19:
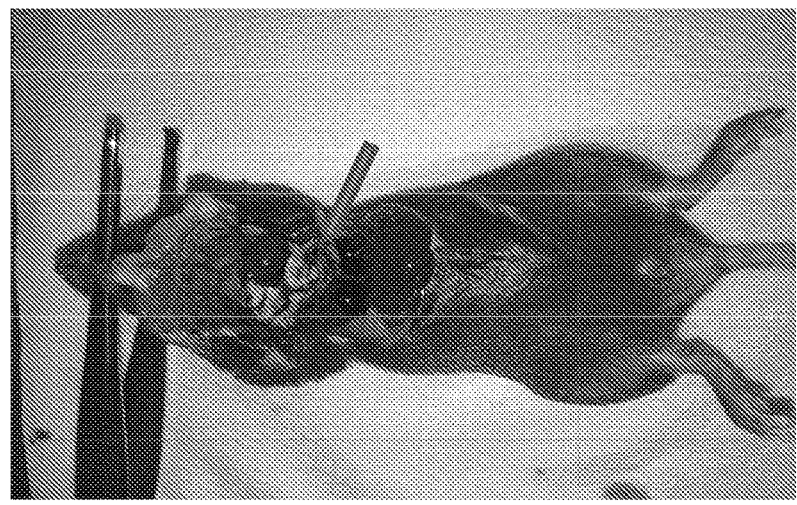
FIG. 19 shows the opened lung and stained with methylene blue.

Ketamine was used to anesthetize the mouse for placement of a tube into the trachea, and a catheter was used for installation of the prepared microparticles. To demonstrate accuracy of pulmonary installation of the microparticles, the lung was stained with methylene blue before killing the mouse. FIG. 19 shows the opened lung with blue color.

The lung tissue was fixed in formalin and cut for histology per protocol. FIG. 5 shows a developed noncaseating granuloma in the mouse lung with H&E staining, and immunohistochemistry staining for CD68, a macrophage marker, and a CD4 marker for PD-L1.

Example 3: *Mycobacterium abscessus* Particle Development

Eight strains of *Mycobacterium abscessus* (MAB) with a rough colony isolated from patients and 2 strains isolated from the environment (isolated from soil) with a smooth colony are used to develop MAB cell wall particles. Each strain contributes 10% portion to the final mix.

MAB is grown in Middlebrook 7H9 broth base with Middlebrook ADC enrichment from Sigma at 37° C. Cells are collected when and optical density of 600 nm (OD600) of 1.0-1.2 is reached by centrifugation at 4000 g for 10 minutes, followed one-time PBS wash, the supernatant is removed and cell pellet is saved for next step. Fifteen to 1 (volume to volume ratio) lysis buffer is added into the tube and sonicated to break down cells. The lysis buffer contains 137 mM Sodium Chloride, 10 mM phosphate, 2.7 mM Potassium Chloride; -combined with detergents and protease inhibitor. Samples are sonicated on ice 30 times. Lysed cells' samples are then centrifuged at 3000 g for 5 minutes to remove possible intact MAB cells. Supernatant is transferred to a new tube and centrifuged for 20 minutes. The pellet is kept and fresh lysis buffer is added. The pellet is resuspended by briefly sonicating and centrifuging at 12,000 g for another 20 minutes. Next, the pellet is kept, mixed with washing buffer, resuspended, and kept in the tube at 95° C. for 15 min. Next, the pellet is allowed to cool down to room temperature and centrifuged at 12,000 g for 20 minutes; next the pellet is kept and washed with PBS buffer 3 times at 12,000 g for 10 minutes. Finally, the pellet is suspended in Dulbecco's Modified Eagle Medium (DMEM) and stored at −80° C.

The concentration of the isolated microparticle is calculated using the following equation: Final concentration=Volume of original culture×OD600×(2.2× $10^8$)/final volume.

Example 4: *Bifidobacterium*: The Most Sensitive Member of Gut Microbiota that Interacts with Pulmonary Sarcoidosis Introduction: Sarcoidosis is a systemic disease of unknown cause that is characterized by the formation of granulomas in multiple organs, mainly lung and mediastinal lymph nodes as a result of dysregulations in host immune system and abnormal collection of inflammatory cells in affected organs. The human immune system and gut microbiome interact synergistically and alteration in respiratory or gastrointestinal tract microbiome have been detected in autoimmune diseases in both humans and animal models, yet few investigated gut microbiota dysbiosis in pulmonary sarcoidosis. The aim of this study was to determine changes in the composition of the gut microbiome in the sarcoidosis mice model.

Methods: Six-week-old age C57Bl/6 male mice were used to develop sarcoid like granulomatous reaction in the lungs. Mice were randomly divided into the experiment (n=4) and control groups (n=3). Experiment groups were challenged intratracheally every 3 days for 4 doses with Mabscessus microparticles using the protocol as described herein. The fecal and cecum samples for each mouse were collected using the Power Soil DNA Isolation Kit (QIAGEN) according to the manufacturer's instructions and processed for DNA extraction. Samples were quantified with Quant-iT dsDNA High Sensitivity Kit and to enrich the fecal DNA for the bacterial 16srRNA V5-V6 rDNA region, DNA was amplified using fusion primers. Each sample was PCR amplified with V5-V6 fusion primers and advanced for sequencing. Microbiome analysis with QIME 1.9.2 was used to calculate alpha diversity and summarize taxa. The relative abundance of species identified through metagenomics pipelines. In addition, GraphPad and Stata15 were used for different statistical analyses.

Results: Instillation of microparticles caused a significant granulomatous inflammatory reaction in the lungs. Microbiome analysis showed a significant reduction in the population of bifidobacteria in fecal (P=0.003633) and cecum samples (P=0.04709). No significant changes in the operational Taxonomic Unit (OTU) were found in the fecal population of *lactobacillus* (P=0.5984).

Conclusions: The results show that in the murine model of sarcoidosis there is a significant change in composition and quantities of gut microbiota. Furthermore, the restoration of gut microbiota can be a therapeutic modality to address the complexity of treatment in sarcoidosis. Bifidobacteria may be more suitable than *lactobacillus* for probiotics therapy in sarcoidosis.

Example 5: Inducible Nitric Oxide Synthase and Nitrotyrosine are Found in the Lung of Sarcoidosis Mice Model Sarcoidosis is an inflammatory disease caused by genetic and environmental triggers. Nitric Oxide (NO) signaling is used by various cells and is important to many biological processes. Inducible nitric oxide is important in the production of the molecule nitric oxide, which is a signaling molecule that is important in the inflammatory response. The role of inducible nitric oxide in sarcoidosis is not well known. It was assessed how Inducible nitric oxide synthase (INOS) is expressed in granulomas in a sarcoidosis mice model.

Methods: Six week old male mice were intratracheally challenged every three to four days with *Mycobacterium abscessus* (MAB) microparticles for 3 weeks. This was done to determine if intratracheal microparticles could initiate the inflammatory response. Immunohistochemistry staining for INOS and nitrotyrosine were performed on the lung tissue sampled in control and microparticle challenged groups. Immunohistochemistry positivity in the lung tissues were scored by a trained lung pathologist. Immunohistochemistry positivity was scored by percentage and intensity from one to three. The percentage of positivity of INOS and nitrotyrosine was compared using nonparametric T-test. Prism was then used to analyze the findings.

Results: Mice that were challenged with MAB microparticles showed granulomatous reaction in lungs. Nitrotyrosine positivity for the three controls were zero percent and had a score of zero. For the experimental group, PART1 showed 70%, PART3 showed 60%, and PART4 showed 40%. The three controls had an intensity of three. INOS stain analysis revealed the positivity for the three controls were zero percent a score of zero. PART1 showed 80% and an intensity of 2, PART2 showed 20% and an intensity of 3.

Conclusion: Challenged mice with microparticles developed granulomatous reaction with significant INOS activity. INOS plays a major role in the production of NO and the inflammatory response in sarcoidosis. These data suggest that inhibiting NO signaling in subjects with sarcoidosis may be a useful treatment strategy.

Example 6: *Mycobacterium abscessus*—Bronchial Epithelial Cells Cross-Talk Through Type 1 Interferon Signaling Introduction: Mycobacteria are aerobic non-motile organisms with lipid rich, hydrophobic cell walls that render them resistant to antibiotics. While there are over 150 different species of nontuberculous mycobacteria (NTM), *Mycobacterium avium* complex (MAC) and *Mycobacterium abscessus* (MAB) are two of the most common culprits of pulmonary infection. MAB has been found to be most common in southeastern United States (Florida to Texas) and the third most rapidly growing NTM infection. It is responsible for chronic lung infections. Mycobacterial cell wall components initiate the interaction between bacteria and host. The reaction between bronchial epithelia and components in the envelope of mycobacterial cell wall is poorly understood.

Methods: A lung-on-membrane model was developed with normal human bronchial epithelial (NHBE) cells re-differentiated at the air-liquid interface (ALI) and human endothelial cells on a Transwell® polyester membrane. Microparticles from MAB cell walls were developed as described herein and added to the ALI side of lung model. NHBE cells were harvested at day 3. RNA was isolated and analyzed with RNASeq. NHBE cells were lysed and protein assay was performed with western blot. It was tested whether lung INF-alpha expression would increase in mice treated with intratracheal MAB cell wall particles. A paired t-test is used to compare two population means using GraphPad Prism 7 software.

Results: RNAseq analysis identified 1759 differentially expressed genes between NHBE cells challenged with and without MAB microparticles with FDR <0.5. 410 genes had a 2.5-fold change (FC) or greater. NHBE cells exposure to MAB microparticles significantly enriched the IFN I signaling pathway. Protein overexpression of IFN I family (2'-5'-Oligoadenylate Synthetase 1, Interferon-induced GTP-binding protein Mx1, Interferon-stimulated gene 15) was found in bronchial epithelial cells following exposure to MAB cell wall microparticles. IFN-α protein and gene expression was significantly increased in mice lung challenged with microparticles in comparison with controls.

Conclusion: These data support the role of Type I IFN in cross-talk between NHBE cells and MAB. They also suggest that initiating immune response by NHBE cells may play a central role in innate immunity. Furthermore, this study underscores the importance of mycobacterial cell wall in initiating innate immune response.

Introduction: Non-tuberculous mycobacteria (NTM) are ubiquitous organisms responsible for clinically significant lung infections that have increased 5-10% annually over the past two decades with an annual burden of ~84,000 cases (Prevots D R, et al., *Clin Chest Med* (2015) 36:13-34). In the United States, *Mycobacterium Avium* Complex (MAC) is the most frequently isolated species followed by *Mycobacterium kansasii* and *Mycobacterium abscessus* (MAB) (Griffith D E, et al., *Am J Respir Crit Care Med.* (2007) 175:367-416). MAB is the most challenging NTM to treat due to high antibiotic resistance rates (Luthra S, et al., *Front Microbiol.* (2018) 9:2179).

Mycobacterial cell walls contain multiple peptidoglycans including D-glucosamine and a mycolic acid layer (Mirsaeidi M, et al, *Ann Am Thorac Soc.* (2015) 12:1278-87) that initiate the interaction between bacteria and host upon inhalation (Reuschl A K, et al., *PLoS Pathog.* (2017) 13:e1006577). Macrophages are an important immune cell in combatting mycobacterial infections with a significant proportion of their response dependent on type I IFN signaling (Monack D M, et al., *Nat Rev Microbiol.* (2004) 2:747-65; and Novikov A, et al., *J Immunol.* (2011) 187: 2540-7). However, the response of bronchial epithelial cells to mycobacterial infection is not well-described. Normal human bronchial epithelial (NHBE) cells express type I IFN that suppress viral replication, induce apoptosis and enhance Th1 immunity (Kalliolias G D, et al. *Arthritis Res Ther.* (2010) 12 (Suppl. 1):S1). NHBE cells exposed to MAB are known to upregulate expression of cytokine transcripts (Matsuyama M, et al., *Am J Respir Cell. Mol Biol.* (2018) 58:241-52). It was tested whether NHBE cells play an important role in initiating the host response to MAB through production of pro-inflammatory type I IFN cytokines. To determine the effects of MAB exposure on NHBE production of type I IFN signaling, the gene expression profile, and protein expression changes in NHBE cell cultures was investigated. The immunologic effects of MAB-cell wall microparticles in lung bronchial and immune cells were tested in a mouse model.

METHODS. Lung-on-Membrane Model (LOMM). As described herein, the dual chamber lung model contains normal human bronchial epithelial (NHBE) cells re-differentiated at the air-liquid interface (ALI) on one side and human endothelial cells (Human Lung Microvascular Endothelial Cells, Lonza, Walkersville, Md.) on the other side of a transwell polyester membrane cell culture inserts (12 mm diameter, 0.4 μm pore size; Corning Life Sciences, Amsterdam, The Netherlands). NHBE cells were collected from lungs rejected for transplant where epithelial cells were isolated from upper bronchi and cultured (Randell S H, et al., *In vitro Cell Dev Biol Anim.* (2001) 37:480-9; Valencia-Gattas M, et al, *PLoS ONE.* (2016) 11:e0160216; and Kunzi L, et al, *Cell Death Discov.* (2019) 5:127). Both sides of the membrane were coated with collagen IV from human placenta (Millipore Sigma, St. Louis, Mo., USA). $5 \times 10^5$ NHBE cells were cultured on top of the membrane in bronchial epithelial cell growth medium (BEGM) until cells were confluent. The cells were placed on air and fed with ALI Media from bottom chamber thereafter. When NHBE cells were fully differentiated and became ciliated, $2 \times 10^5$ endothelial cells were plated on the opposite side of the transwell membrane when membrane was upside down. The upside-down membrane was placed into humidified incubator at 3TC, 5% $CO_2$ for 8 h to let endothelial cells to adhere. The transwell was flipped to the original position and both cells lines were feed with a 50:50 mixture of endothelial and epithelia cell media in the bottom chamber and were incubated for 24 h. NHBE cells were washed and the media was changed every 2 days. Two days after adding the endothelial cells, the lung model was used for experiment and the media was changed every 2 days. This lung model has been previously published (Korukonda A Z C, et al, *Am J Respir Cell Mol Biol.* (2019) 60:717-9). For the current study, primary NHBE cells from five individuals were used to develop LOMM. Table 1 shows demographic data and smoking history of lung donors.

TABLE 1

| Age, race and smoking history of lung donors. | | | |
|---|---|---|---|
| Subjects | Age | Race | Smoking |
| 1 | 60-65 | European American | NS |
| 2 | 65-70 | Latino | NS |
| 3 | 75-80 | European American | NS |
| 4 | 20-25 | Latino | NS |
| 5 | 35-40 | European American | NS |

MAB Microparticle Production. MAB cell wall microparticles were isolated from a strain of MAB with a rough colony isolated from the sputum of an 11-year old boy with cystic fibrosis (isolate # CCUG 47942). MAB is grown in Middlebrook 7H9 broth with ADC enrichment medium (Millipore Sigma, St. Louis, Mo., USA) at 3TC. When the culture OD600 reached 1.0-1.2, cells were collected by centrifugation at 4,000 g for 10 min, washed once in PBS, centrifuged, resuspended using a 15:1 (volume to volume) ratio of lysis buffer, sonicated and incubated on ice for 30 min. The lysis buffer contains 137 mM sodium chloride, 10 mM sodium phosphate, 2.7 mM potassium chloride, and detergents and protease inhibitors. Lysed cell samples were then centrifuged at 3,000 g for 5 min to remove intact MAB cells. The supernatant was transferred to a new tube and centrifuged for 20 min. Twenty milliliters of fresh lysis buffer was added and the pellet was resuspended by brief sonication and centrifuged at 12,000 g for another 20 min. The pellet was resuspended in 20 ml volume of PBS and kept at 95° C. for 15 min. After cooling to room temperature, the lysate was centrifuged at 12,000 g for 20 min and the pellet was washed with PBS buffer 3 times at 12,000 g for 10 min. Finally, the pellet is suspended in Dulbecco's Modified Eagle Medium (DMEM) and stored at −80° C. The concentration of the microparticles is calculated by the following equation: Final concentration=Volume of original culture×OD600×$(2.2 \times 10^8$ bacteria/ml)/final volume. High quality images of MAB particles were obtained by scanning electron microscope (SEM) and proven to be non-infectious by absence of growth of MAB in culture.

Exposure of Epithelial Cells to MAB Microparticles. LOMM (bronchial epithelial cells side) were exposed to 100 μL of MAB microparticles diluted to a concentration equal to a multiplicity of infection (whole bacterium) of 10:1. Bronchial epithelial cells were harvested 72 h after exposure.

Mouse Model Exposure to MAB Microparticles. Six-week-old age C57Bl/6 male mice purchased from the Jackson Laboratory (Bar Harbor, Me.) in experiments. Individual mice were challenged intratracheally every 3 days with MAB microparticles for 4 doses using a 20 G angiocatheter inserted into the trachea. After tube placement, microparticles were injected with the first dose injecting 50 μL (~$5 \times 10^8$ CFU) and next three doses receiving 20 μL (~$2 \times 10^8$ of CFU). The control group received equivalent volumes of PBS intratracheally.

Mice were sacrificed on day 14 and the left lungs were harvested for pathology after perfusion to remove blood. Lungs were filled with 10% buffered formalin and fixed in formalin for at least 72 h before immunohistochemistry (IHC) staining. H&E staining was used to determine inflammatory pathology. Lungs were stained with antibodies against CD4 (rabbit, Abcam, catalogue # ab133616), CD8 (rabbit, Abcam, #ab12512), CD68 (rabbit, Abcam, #ab12512), PD-L1(rabbit, Proteintech, #17952-1-AP), and IFN-α (rabbit, Abcam, #ab193055) antibodies to identify infiltrating immune cells. Lung inflammation was scored using the three fields with the highest infiltrate's intensity at 100× power magnification. The area of inflammation was measured and averaged for the three examined high power fields. The right lungs were removed and frozen at −80° C. for later protein extraction and western blot analysis. Protein extracted from lung tissue was performed (Decaris M L, et al, *Mol Cell Proteomics*. (2014) 13:1741-52).

RNAseq and Pathway Analysis. Total RNA from NHBE cells was extracted by using a Direct-zol™ RNA MicroPrep kit (R2060, Zymo Research Zymo Research, Irvine, Calif.), following the manufacturer's protocol. Briefly, cells were washed with PBS, lysed in TRI reagent and RNA was purified using a Direct-zol RNA column. DNase I treatment was performed on the column and RNA was eluted in DNase/Rnase Free water.

RNA from mouse lungs were extracted using RNA Miniprep Plus Kit (Zymo Research). Briefly, whole lung was homogenized in TRI reagent and total RNA extraction was performed following the instructions provided by the manufacturer with additional DNase treatment. Quantity and quality of the samples was determined by NanoDrop spectrophotometer and Agilent Bioanalyzer 2100, respectively. Samples with RNA integrity number >8 were used for the analysis.

Preparation and sequencing of RNA libraries was performed. Briefly, total RNA quantity and quality were determined using the Agilent Bioanalyzer. At least 300 ng of total RNA was used as input for the KAPA RNA HyperPrep Kit with RiboErase (HMR) according to manufacturer's protocol to create ribosomal RNA-depleted sequencing libraries. Sequencing was performed on the Illumina NextSeq 500 generating ~40 million single-end 75 base reads per sample. Sequencing data were processed with a bioinformatics pipeline including quality control, alignment to the hg19 human reference genome, and gene quantification. Count data was inputted into edgeR software (Shamaei M P M, et al., *Sarcoidosis Vasculitis and Diffuse Lung Disease* 2018; 34 236-241) for differential expression analysis. Counts were normalized using the trimmed mean of M-values (TMM) method (Facco M, et al., *Thorax* 2011; 66: 144-150) to account for compositional difference between the libraries and paired differential expression analysis using a generalized linear model with sample as a blocking factor. Genes were considered statistically different with a false discovery rate p-value (FDR)<0.05.

Pathway enrichment analyses was performed using Enrichr online (Tsiligianni I, et al., *BMC pulmonary medicine* 2005; 5: 8) and DAVID bioinformatics resource (Prasse A, et al., *Clinical and experimental immunology* 2000; 122: 241-248) to obtain the enriched biological processes (BPs) and pathways with genes with a linear fold change (FC)>2.5.

Western Blotting. NHBE cells and lung tissue cells were lysed in lysis buffer (Cell Signaling Technology, Beverly, Mass.) with protease inhibitor cocktail (Cell Signaling Technology, Beverly, Mass.) and sonicated three times for 2 s each with at least 1-min rest on ice between each 2-s pulse. Samples were centrifuged at 10,000×g for 5 min at 4° C. and the supernatant was collected. Protein concentration was determined by BCA protein assay kit from Cell Signaling Technology.

Thirty micrograms of total protein were mixed in a reducing sample buffer, and then electrophoresed on a 10-15% Tris gel with Tris running buffer, blotted to PVDF membrane, and sequentially probed with primary antibodies against 2'-5'-Oligoadenylate Synthetase 1 (OAS1), Interferon-induced GTP-binding protein Mx1 (MX1), Interferon-stimulated gene 15 (ISG15) (Proteintech Group, Inc. Rosemont, Ill.). A horseradish peroxidase-conjugated goat anti-rabbit antibody was then added, and secondary antibodies were detected using enhanced chemiluminescence (ECL Plus, General Electric Healthcare, and Milwaukee, Wis.).

Statistical Analysis. A paired t-test is used to compare two population means using GraphPad Prism 7 software. Results with p<0.05 were defined as statistically significant.

RESULTS. IFN I Signaling Pathway Genes Are Overexpressed in NHBE Cells Following MAB Exposure. The MAB cell wall particles with a size that ranged from less than a sub-micron to 2 μm were exposed to NHBE cells and RNA and protein expression was analyzed. RNAseq analysis identified 1759 differentially expressed genes between NHBE cells challenged with and without MAB microparticles (FDR <0.5) and found 410 genes had at least a 2.5-fold change (FC). Volcano plots show marked differences in gene expression between NHBE cells with and without exposure to MAB microparticles and a heatmap shows the unsupervised clustering of the RNAseq transcriptomes according to pearson correlation. Individual gene expression was normalized across samples to percentages ranging from marked downregulation to marked upregulation.

The pathway enrichment analysis for gene differentially expressed 2.5 fold between NHBE cells with and without exposure to MAB microparticles. NHBE cells exposure to MAB microparticles significantly enriched the IFN I signaling pathway (GO:0060337) and cellular response to type I IFN (GO:0071357) (adjusted p=0.00001047, and p=0.00001047 respectively) in pathway analysis (Table 2). The top upregulated genes from the IFN I family (with FC>2.5 and FDR<0.5) were Radical S-Adenosyl Methionine Domain Containing (RSAD2) (FC 6.67), Myxovirus resistance 2 (MX2) (FC 5.66), Interferon induced protein 44 like (IFI44L) (FC 4.34), Interferon stimulated gene (ISG)15 (FC 4.34), Interferon Induced Protein With Tetratricopeptide Repeats 1 (IFIT1) (FC 4.20), Interferon Alpha Inducible Protein 6 (IFI) (FC 3.66), MX1 (FC 3.1), 2'-5'-Oligoadenylate Synthetase (OAS)1 (FC 2.79), and OAS3 (FC 2.69). Increased protein expression of MX1, OSA1, and ISG15 was confirmed using western blot in cultures exposed to MAB microparticles.

TABLE 2

The pathway enrichment analysis for gene differentially expressed 2.5 fold between NHBE cells with and without exposure to MAB microparticles.

| Index | Name | P-value | Adjusted p-value |
|-------|------|---------|------------------|
| 1 | Epidermal cell differentiation (GO:0009913) | 8.304e−13 | 9.309e−10 |
| 2 | Peptide cross-linking (GO:0018149) | 5.967e−12 | 2.230e−9 |
| 3 | Type I interferon signaling pathway (GO:0060337) | 6.54e−8 | 0.00001047 |
| 4 | Keratinocyte differentiation (GO:0030216) | 3.633e−12 | 2.037e−9 |
| 5 | Epidermis development | 2.621e−9 | 5.876e−7 |
| 6 | Regulation of nuclease activity (GO:0032069) | 0.00005144 | 0.004436 |
| 7 | Skin development (GO:0043588) | 9.947e−10 | 2.788e−7 |
| 8 | Negative regulation of viral genome replication (GO:045071) | 1.165e−7 | 0.00001632 |
| 9 | Cellular response to type I interferon (GO:0071357) | 6.541e−8 | 0.00001047 |
| 10 | Negative regulation of viral life cycle (GO:1903901 | 5.545e−7 | 0.00006907 |

Overexpression of Cytokine Genes in NHBE Cells Following MAB Exposure. Cytokine genes expression profile of NHBE cells following exposure to MAB cell wall microparticles also showed significant upregulation of IL36β (FC 41.3), IL36α (FC 18.4), IL36γ (FC 3.2), IL 23A (FC 3.2), IL1RL1 (FC 3.1), IL1RN (FC 3.1), and IL1RN (FC 2.6). Chemokine profiles showed significant expressions of CCL5 (FC 8.8), CXCL11 (FC 3.1), CCL22 (FC 2.8), and CXCL10 (FC 2.5). It was also found Matrix Metallopeptidase (MMP) 9 (FC4) was differentially expressed between two groups.

Figure 20:
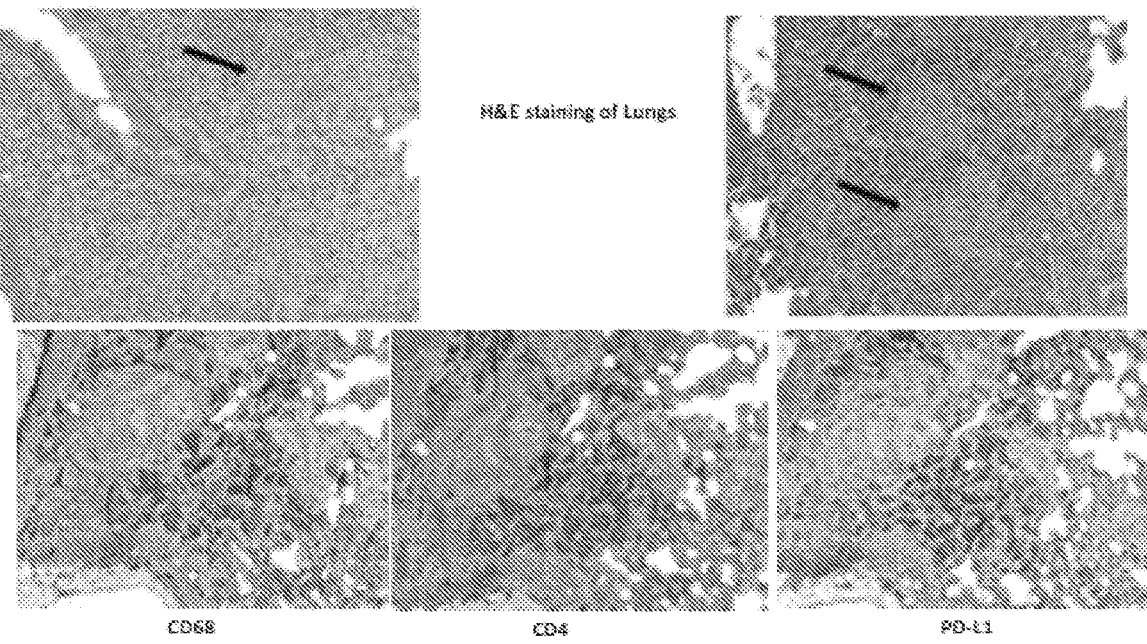
FIG. 20 shows developed noncaseating granuloma in the mouse lung with H&E staining (black arrows), and immunohistochemistry staining for CD68, a macrophage marker, and CD4, a marker for PD-L1.

Granulomatous Reaction in the Lungs Following Exposure to MAB. FIG. 20 shows mouse lungs developed non-caseating granuloma after MAB microparticles challenge. The inflammatory lesions were scored and showed significant increase in inflammation by H&E staining with marked increase in cells staining for macrophage marker, CD68, and PD-L1. IHC staining for IFN-α also showed significant increasing in bronchial cells in comparison with controls (P<0.00001).

IFN I Signaling Pathway Genes Are Overexpressed in Mouse Lungs Following Exposure to MAB. RNAseq analysis identified 1759 differentially expressed genes between NHBE cells challenged with and without MAB microparticles with FDR <0.5, 1155 genes had a 2.5-fold change (FC) or greater. Volcano plots reveal differential expression of genes between NHBE cells with and without exposure to MAB microparticles and a heatmap shows unsupervised clustering of the RNAseq transcriptomes according to pearson correlation. Gene expression for each gene was normalized across samples to percentages ranging from marked upregulation to marked downregulation. Many immunogens were significantly upregulated in challenged mice by MAB microparticles. Significant upregulation of IL-17a and IL-17f genes in mice lung after exposure to microparticles was detected.

Pathway enrichment analysis for selected genes with a FDR<0.05 differentially expressed between mice lung cells treated with saline (control) vs. MAB microparticles. MAB microparticle challenged lungs significantly showed gene pathway enrichment in the type I interferon pathway (GO: 0071357) and type I IFN signaling pathway (GO:0060337) (adjusted p=1.757e-19, and p=8.783e-20, respectively). The top upregulated genes from the IFN I family were IRF1 (FC:2.54), IFIT3 (FC:2.55), ISG15 (FC:2.56), MXD3 (FC: 3), IRF8 (FC:3.05), and MX1 (FC:3.10).

IFN-α Proteins Overexpression in the Lungs Following Exposure to MAB. Expression of IFN-α in bronchial and granulomatous inflammatory cells were significantly increased following exposure to MAB cell wall microparticles (P<0.00001). Western blot analysis of IFN-α protein expression found significant increase in microparticle challenged lung tissue (P=0.0002) compared to negative controls.

DISCUSSION This study found upregulation of 11 genes of the IFN 1 signaling pathway, upregulation of the 3 species of IL-36 (α, β, and γ) and upregulation of leukocyte chemokines in NHBE cells after exposure to microparticles of MAB. Mouse lungs challenged with MAB cell wall microparticles showed a granulomatous reaction with significant upregulation of IFN 1 genes. It was also demonstrated that protein expression of MX1, OSA1, ISG15, and IFN-α were upregulated after MAB-host interaction in in vitro and in vivo models. IL-17a and IL-17f were upregulated in mice lung after exposure to microparticles. These data show MAB cell walls elicit a proinflammatory reaction from NHBE cells that likely initiates the host response to MAB infection. Finding similar gene expression changes in mice exposed to MAB particles confirms the bronchial epithelia response in an intact organism.

IFN I genes play an important role in controlling viral infections in bronchial epithelia and the results described herein implicate their role in the host response to mycobacterial disease. IFIT1, ISG15, ISG20, and OAS 1, 2, and 3 inhibit protein synthesis and cell proliferation in viral infected host cells. MX1 protein inhibits viral nucleoprotein synthesis and endocytosis (Wen A Y, et al., *Journal of immunology* 2010; 185: 6413-6419). Given that mycobacteria are also intracellular pathogens, IFN response genes may also form the first layer of innate defense in upregulating macrophage and T cell specific genes including IL-17.

NHBE cells treated with MAB microparticles significantly upregulated the three subtypes of IL36 (α, β, and γ). IL36 belongs to the IL1 superfamily and is expressed by bronchial epithelial cells. IL-36 activates the pro-inflammatory transcriptional factor nuclear factor kappa B (NFkB), induces T Helper cell type 1 (Th1) responses by enhancing cell proliferation and IL2 secretion (Nagai S, et al., *Clinics in chest medicine* 2008; 29: 565-574; and Iannuzzi M C, et al., *JAMA*, 2011; 305: 391-399) and is implicated in the inflammatory response from skin epithelial cells in psoriasis (Lockstone H E, et al., *American journal of respiratory and critical care medicine* 2010; 181: 1367-1375). IL36 is known to control IFN I related gene expression in a time dependent manner (Zhang S, et al., *Laboratory investigation; a journal of technical methods and pathology* 1999; 79: 395-405) and may play a role in NHBE response to MAB cell wall components. The in vitro study also showed a significant upregulation in IL-36 genes and members of the IL1 superfamily genes suggesting a possible link between IL-36 expression from NHBE cells leading to type I IFN gene expression via autocrine loop.

MAB exposed NHBE also produced chemokines CCL5 and CCL22 that are strong leukocyte chemoattractants. The gene of both chemokines were upregulated in the mice lung after challenging with MAB cell wall microparticle. CCL5 is a potent monocyte and macrophage attractant recruiting important immune cells to combat mycobacterial infections. The immune response to MAB is T cell dependent and that macrophages develop pathologic features of mycobacterial disease known as granulomas. Significant granulomatous reaction was found in the lung of challenged mice that could suggest functional activity of upregulated CCL5 and CCL22. Interestingly, MMP9 is an important protein required to recruit macrophages and develop well organized granulomas in MTB infections (Crouser E D, et al., *American journal of respiratory cell and molecular biology* 2017; 57: 487-498). Thus, NHBE expression of MMP may also initiate the granuloma formation commonly seen in mycobacterial infections.

These data strongly support the role of NHBE cells in the host defense against MAB infections. They suggest that bronchial epithelial cells play a central role in initiating an innate immune response producing the initial signal alerting resident macrophages to the site of infection and producing IL36 and type I IFN genes to add to the host defense. Furthermore, this study underscores the importance of mycobacterial cell wall antigens in initiating the innate immune response. Understanding the direct impact of the IFN I genes and IL36 production by NHBE cells during MAB infection will provide data to develop strategies to treat or prevent NTM infections.

What is claimed is:

1. A method of producing a *Mycobacterium abscessus* cell wall microparticle, the method comprising:

(a) obtaining cells from a rough colony of one or more strains of *Mycobacterium abscessus;*

(b) lysing the cells in a lysis buffer, wherein the lysis buffer comprises a protease inhibitor and a detergent;

(c) centrifuging the cells in (b) so as to produce a pellet and a supernatant liquid; and collecting the supernatant;

(d) centrifuging the supernatant so as to produce a second pellet and a second supernatant liquid; and collecting the second pellet; and (e) contacting the second pellet with a lysis buffer and heating to a temperature of at least 90° C., wherein the lysis buffer comprises a protease inhibitor and a detergent;

thereby forming *Mycobacterium abscessus* cell wall microparticles.

2. The method of claim 1, further comprising adding cells from a smooth colony of one or more strains of *Mycobacterium abscessus* to the cells of step (a) prior to step (b).

3. The method of claim 2, wherein the ratio of strains of *Mycobacterium abscessus* from a rough colony to the strains of *Mycobacterium abscessus* from a smooth colony is 2:1, 3:1, 4:1 or 5.1.

4. The method of claim 1, wherein the cells from the rough colony are from a sample from a subject infected with *Mycobacterium abscessus.*

5. The method of claim 2, wherein the cells from the smooth colony are from an environmental sample.

6. The method of claim 1, further comprising collected one or more cells in step (a) after having reached an optical density at 600 nm between 1.0 and 1.2 before the lysing in step (b).

7. The method of claim 1, wherein the *Mycobacterium abscessus* cell wall microparticles can form a granuloma.

8. The method of claim 7, wherein the granuloma expresses one or more T helper cell markers.

* * * * *